(12) United States Patent
Plowman et al.

(10) Patent No.: US 8,105,785 B2
(45) Date of Patent: Jan. 31, 2012

(54) MYLKS AS MODIFIERS OF BRANCHING MORPHOGENESIS AND METHODS OF USE

(75) Inventors: Gregory D. Plowman, San Carlos, CA (US); Felix D. Karim, Walnut Creek, CA (US); Candace Swimmer, San Francisco, CA (US); Hinrich Alexander Habeck, Tuebingen (DE); Thomas I. Koblizek, Tuebingen (DE); Stefan Schulte-Merker, Utrecht (DE); Ulrike Eisenmann, Tutzig (DE); Gordon Mark Stott, San Francisco, CA (US); Torsten Trowe, San Francisco, CA (US); Andreas Michael Vogel, Basel (CH); Joerg Heinrich Odenthal, Tuebingen (DE); Jochen Konrad Scheel, San Carlos, CA (US); Torsten Tilmann Will, Bielefeld (DE); Yinsheng Jin, Pinceton, NJ (US); Lynn Margaret Bjerke, Sutton (GB); Timothy S. Heuer, El Granada, CA (US)

(73) Assignee: Exelixis, Inc., South San Francisco, CA (US)

( * ) Notice: Subject to any disclaimer, the term of this patent is extended or adjusted under 35 U.S.C. 154(b) by 1246 days.

(21) Appl. No.: 10/556,637

(22) PCT Filed: Jun. 18, 2004

(86) PCT No.: PCT/US2004/019485
§ 371 (c)(1),
(2), (4) Date: Mar. 20, 2007

(87) PCT Pub. No.: WO2005/003372
PCT Pub. Date: Jan. 13, 2005

(65) Prior Publication Data
US 2008/0317738 A1    Dec. 25, 2008

Related U.S. Application Data

(60) Provisional application No. 60/479,781, filed on Jun. 19, 2003.

(51) Int. Cl.
*C12Q 1/68*    (2006.01)
*G01N 33/53*    (2006.01)
(52) U.S. Cl. ........................ 435/6.14; 435/7.1
(58) Field of Classification Search .................. None
See application file for complete search history.

(56) References Cited

U.S. PATENT DOCUMENTS
2006/0269921 A1 *  11/2006  Segara et al. ............... 435/6

FOREIGN PATENT DOCUMENTS
WO    WO 02/24889    *    3/2002
WO    WO 03/045321         6/2003

OTHER PUBLICATIONS

Klemke et al, J Cell Biol. Apr. 21, 1997;137(2):481-92.*
Porkka et al; Journal of Pathology, vol. 193, pp. 73-79; 2001.*
Ramaswamy et al; Nature Genetics, vol. 33, pp. 49-54, Dec. 2002.*
Young Hwa Soung et al.: "Mutational analysis of the kinase domain of MYLK2 gene in common human cancers," Pathology—Research and Practice 202 (2006), pp. 137-140.
Yagi et al. Identification of an activator protein for myosin light chai kinase as the $Ca^{2+}$-dependent modulator protein. J. Biol. Chem. Mar. 1978, vol. 253, No. 5, pp. 1338-1340, see entire document.
Kenzo et al.: "Myosin light chain kinase inhibitors can block invasion and adhesion of human pancreatic cell lines" Pancreas, vol. 24, No. 1, 2002, pp. 34-41.

* cited by examiner

*Primary Examiner* — James Martinell
(74) *Attorney, Agent, or Firm* — McDonnell Boehnen Hulbert & Berghoff LLP

(57) ABSTRACT

Human MYLK genes are identified as modulators of branching morphogenesis, and thus are therapeutic targets for disorders associated with defective branching morphogenesis function. Methods for identifying modulators of branching morphogenesis, comprising screening for agents that modulate the activity of MYLK are provided.

5 Claims, No Drawings

MYLKS AS MODIFIERS OF BRANCHING MORPHOGENESIS AND METHODS OF USE

REFERENCE TO RELATED APPLICATIONS

This application is a U.S. National Stage Application of PCT/US04/19485, filed Jun. 18, 2004, which claims priority to U.S. provisional patent application 60/479,781 filed Jun. 19, 2003. The contents of these applications are hereby incorporated by reference in their entireties.

BACKGROUND OF THE INVENTION

Several essential organs (e.g., lungs, kidney, lymphatic system and vasculature) are made up of complex networks of tube-like structures that serve to transport and exchange fluids, gases, nutrients and waste. The formation of these complex branched networks occurs by the evolutionarily conserved process of branching morphogenesis, in which successive ramification occurs by sprouting, pruning and remodeling of the network. During human embryogenesis, blood vessels develop via two, processes: vasculogenesis, whereby endothelial cells are born from progenitor cell types; and angiogenesis, in which new capillaries sprout from existing vessels.

Branching morphogenesis encompasses many cellular processes, including proliferation, survival/apoptosis, migration, invasion, adhesion, aggregation and matrix remodeling. Numerous cell types contribute to branching morphogenesis, including endothelial, epithelial and smooth muscle cells, and monocytes. Gene pathways that modulate the branching process function both within the branching tissues as well as in other cells, e.g., certain monocytes can promote an angiogenic response even though they may not directly participate in the formation of the branch structures.

An increased level of angiogenesis is central to several human disease pathologies, including rheumatoid arthritis and diabetic retinopathy, and, significantly, to the growth, maintenance and metastasis of solid tumors (for detailed reviews see Liotta L A et al, 1991 Cell 64:327-336; Folkman J., 1995 Nature Medicine 1:27-31; Hanahan D and Folkman J, 1996 Cell 86:353-364). Impaired angiogenesis figures prominently in other human diseases, including heart disease, stroke, infertility, ulcers and scleroderma.

The transition from dormant to active blood vessel formation involves modulating the balance between angiogenic stimulators and inhibitors. Under certain pathological circumstances an imbalance arises between local inhibitory controls and angiogenic inducers resulting in excessive angiogenesis, while under other pathological conditions an imbalance leads to insufficient angiogenesis. This delicate equilibrium of pro- and anti-angiogenic factors is regulated by a complex interaction between the extracellular matrix, endothelial cells, smooth muscle cells, and various other cell types, as well as environmental factors such as oxygen demand within tissues. The lack of oxygen (hypoxia) in and around wounds and solid tumors is thought to provide a key driving force for angiogenesis by regulating a number of angiogenic factors, including Hypoxia Induced Factor alpha (HIF1 alpha) (Richard D E et al., Biochem Biophys Res Commun. 1999 Dec. 29; 266(3):718-22). HIF1 in turn regulates expression of a number of growth factors including Vascular Endothelial Growth Factor (VEGF) (Connolly D T, J Cell Biochem 1991 November; 47(3):219-23). Various VEGF ligands and receptors are vital regulators of endothelial cell proliferation, survival, vessel permeability and sprouting, and lymphangiogenesis (Neufeld G et al., FASEB J 1999 January; 13(1):9-22; Stacker S A et al., Nature Medicine 2001 7:186-191; Skobe M, et al., Nature Medicine 2001 7:192-198; Makinen T, et al., Nature Medicine 2001 7:199-205).

Most known angiogenesis genes, their biochemical activities, and their organization into signaling pathways are employed in a similar fashion during angiogenesis in human, mouse and Zebrafish, as well as during branching morphogenesis of the *Drosophila* trachea. Accordingly, *Drosophila* tracheal development and zebrafish vascular development provide useful models for studying mammalian angiogenesis (Sutherland D et al., Cell 1996, 87:1091-101; Roush W, Science 1996, 274:2011; Skaer H., Curr Biol 1997, 7:R238-41; Metzger R J, Krasnow M A. Science. 1999. 284:1635-9; Roman B L, and Weinstein B M. Bioessays 2000, 22:882-93).

The contraction of smooth muscle begins with the phosphorylation of the light chain of myosin, a reaction catalyzed by myosin light chain kinase (MYLK) that is itself activated by the binding of calcium-calmodulin. MYLK exists in both nonmuscle and smooth muscle isoforms, where the various isoforms are encoded by differential use of 31 coding exons (Lazar, V., and Garcia, J. G. N. (1999) Genomics 57: 256-267; Watterson D M et al. (1999) J. Cell. Biochem.).

The ability to manipulate and screen the genomes of model organisms such as *Drosophila* and zebrafish provides a powerful means to analyze biochemical processes that, due to significant evolutionary conservation of genes, pathways, and cellular processes, have direct relevance to more complex vertebrate organisms.

Short life cycles and powerful forward and reverse genetic tools available for both Zebrafish and *Drosophila* allow rapid identification of critical components of pathways controlling branching morphogenesis. Given the evolutionary conservation of gene sequences and molecular pathways, the human orthologs of model organism genes can be utilized to modulate branching morphogenesis pathways, including angiogenesis.

All references cited herein, including patents, patent applications, publications, and sequence information in referenced Genbank identifier numbers, are incorporated herein in their entireties.

SUMMARY OF THE INVENTION

We have discovered genes that modify branching morphogenesis in zebrafish, and identified their human orthologs, hereinafter referred to as Myosin Light Chain Kinase (MYLK). The invention provides methods for utilizing these branching morphogenesis modifier genes and polypeptides to identify MYLK-modulating agents that are candidate therapeutic agents that can be used in the treatment of disorders associated with defective or impaired branching morphogenesis function and/or MYLK function. Preferred MYLK-modulating agents specifically bind to MYLK polypeptides and restore branching morphogenesis function. Other preferred MYLK-modulating agents are nucleic acid modulators such as antisense oligomers and RNAi that repress MYLK gene expression or product activity by, for example, binding to and inhibiting the respective nucleic acid (i.e. DNA or mRNA).

MYLK modulating agents may be evaluated by any convenient in vitro or in vivo assay for molecular interaction with a MYLK polypeptide or nucleic acid. In one embodiment, candidate MYLK modulating agents are tested with an assay system comprising a MYLK polypeptide or nucleic acid. Agents that produce a change in the activity of the assay system relative to controls are identified as candidate branching morphogenesis modulating agents. The assay system may be cell-based or cell-free. MYLK-modulating agents include MYLK related proteins (e.g. dominant negative mutants, and biotherapeutics); MYLK-specific antibodies; MYLK-specific antisense oligomers and other nucleic acid modulators; and chemical agents that specifically bind to or interact with MYLK or compete with MYLK binding partner (e.g. by binding to a MYLK binding partner). In one specific embodiment, a small molecule modulator is identified using a kinase assay. In specific embodiments, the screening assay system is selected from a binding assay, an apoptosis assay, a cell proliferation assay, an angiogenesis assay, a hypoxic induction assay, a tubulogenesis assay, a cell adhesion assay, and a sprouting assay.

In another embodiment of the invention, the assay system comprises cultured cells or a non-human animal expressing MYLK, and the assay system detects an agent-biased change in branching morphogenesis, including angiogenesis. Events detected by cell-based assays include cell proliferation, cell cycling, apoptosis, tubulogenesis, cell migration, and response to hypoxic conditions. For assays that detect tubulogenesis or cell migration, the assay system may comprise the step of testing the cellular response to stimulation with at least two different pro-angiogenic agents. Alternatively, tubulogenesis or cell migration may be detected by stimulating cells with an inflammatory angiogenic agent. In specific embodiments, the animal-based assay is selected from a matrix implant assay, a xenograft assay, a hollow fiber assay, or a transgenic tumor assay.

In another embodiment, candidate branching morphogenesis modulating agents that have been identified in cell-free or cell-based assays are further tested using a second assay system that detects changes in an activity associated with branching morphogenesis. In a specific embodiment, the second assay detects an agent-biased change in an activity associated with angiogenesis. The second assay system may use cultured cells or non-human animals. In specific embodiments, the secondary assay system uses non-human animals, including animals predetermined to have a disease or disorder implicating branching morphogenesis, including increased or impaired angiogenesis or solid tumor metastasis.

The invention further provides methods for modulating the MYLK function and/or branching morphogenesis in a mammalian cell by contacting the mammalian cell with an agent that specifically binds a MYLK polypeptide or nucleic acid. The agent may be a small molecule modulator, a nucleic acid modulator, or an antibody and may be administered to a mammalian animal predetermined to have a pathology associated branching morphogenesis.

DETAILED DESCRIPTION OF THE INVENTION

Genetic screens were designed to identify modifiers of branching morphogenesis in zebrafish. We used a screen based on antisense technologies to identify genes whose disruption produced vascular defects in zebrafish. Briefly, and as further described in the Examples, one-cell stage embryos were treated with antisense morpholino oligonucleotides (PMOs) that targeted a large number of predicted zebrafish genes. Treated animals were fixed at the larval stage, and alkaline phosphatase staining was used to visualize blood vessel formation. The zebrafish DR-MYLK gene (SEQ ID NO:10) was identified as a modifier of branching morphogenesis. Accordingly, vertebrate orthologs of these modifiers, and preferably the human orthologs, MYLK genes (i.e., nucleic acids and polypeptides) are attractive drug targets for the treatment of pathologies associated with a defective branching morphogenesis signaling pathway, such as cancer.

In vitro and in vivo methods of assessing MYLK function are provided herein. Modulation of the MYLK or their respective binding partners is useful for understanding the association of branching morphogenesis and its members in normal and disease conditions and for developing diagnostics and therapeutic modalities for branching morphogenesis related pathologies. MYLK-modulating agents that act by inhibiting or enhancing MYLK expression, directly or indirectly, for example, by affecting a MYLK function such as enzymatic (e.g., catalytic) or binding activity, can be identified using methods provided herein. MYLK modulating agents are useful in diagnosis, therapy and pharmaceutical development.

As used herein, branching morphogenesis encompasses the numerous cellular process involved in the formation of branched networks, including proliferation, survival/apoptosis, migration, invasion, adhesion, aggregation and matrix remodeling. As used herein, pathologies associated with branching morphogenesis encompass pathologies where branching morphogenesis contributes to maintaining the healthy state, as well as pathologies whose course may be altered by modulation of the branching morphogenesis.

Nucleic Acids and Polypeptides of the Invention

Sequences related to MYLK nucleic acids and polypeptides that can be used in the invention are disclosed in Genbank (referenced by Genbank identifier (GI) number) as GI#s 16950600 (SEQ ID NO:1), 6950610 (SEQ ID NO:2), 16950612 (SEQ ID NO:3), 16950614 (SEQ ID NO:4), 16950616 (SEQ ID NO:5), 16950618 (SEQ ID NO:6), 16950620 (SEQ ID NO:7), 16950622 (SEQ ID NO:8), 16950624 and (SEQ ID NO:9), and GI#16950611 (SEQ ID NO:11) for polypeptide sequences.

The term "MYLK polypeptide" refers to a full-length MYLK protein or a functionally active fragment or derivative thereof. A "functionally active" MYLK fragment or derivative exhibits one or more functional activities associated with a full-length, wild-type MYLK protein, such as antigenic or immunogenic activity, enzymatic activity, ability to bind natural cellular substrates, etc. The functional activity of MYLK proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active MYLK polypeptide is a MYLK derivative capable of rescuing defective endogenous MYLK activity, such as in cell based or animal assays; the rescuing derivative may be from the same or a different species. For purposes herein, functionally active fragments also include those fragments that comprise one or more structural domains of a MYLK, such as a kinase domain or a binding domain. Protein domains can be identified using the PFAM program (Bateman A., et al., Nucleic Acids Res, 1999, 27:260-2). For example, the kinase domain (PFAM 00069) of MYLK from GI#16950611 (SEQ ID NO:11) is located at approximately amino acid residues 1464 to 1719. Likewise, the Immunoglobulin domain (PF00047) of the same protein is located at approximately amino acid residues 47 to 108, 175 to 235, 428 to 489, 528 to 585, 637 to 697, 735 to 796, 1112 to 1172, 1252 to 1312, and 1823 to 1884. Methods for obtaining MYLK polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a MYLK. In further preferred embodiments, the fragment comprises the entire functionally active domain.

The term "MYLK nucleic acid" refers to a DNA or RNA molecule that encodes a MYLK polypeptide. Preferably, the MYLK polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human MYLK. Methods of identifying orthlogs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10: 1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as zebrafish, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6): 6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a MYLK. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a MYLK under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% FICOLL®, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% FICOLL®, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of MYLK Nucleic Acids and Polypeptides MYLK nucleic acids and polypeptides, are useful for identifying and testing agents that modulate MYLK function and for other applications related to the involvement of MYLK in branching morphogenesis. MYLK nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a MYLK protein for assays used to assess MYLK function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant MYLK is expressed in a cell line known to have defective branching morphogenesis function. The recombinant cells are used in cell-based screening assay systems of the invention, as described further below.

The nucleotide sequence encoding a MYLK polypeptide can be inserted into any appropriate expression vector. The necessary transcriptional and translational signals, including promoter/enhancer element, can derive from the native MYLK gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the MYLK gene product, the expression vector can comprise a promoter operably linked to a MYLK gene nucleic acid, one or more origins of replication, and, one or more selectable markers (e.g. thymidine kinase activity, resistance to antibiotics, etc.). Alternatively, recombinant expression vectors can be identified by assaying for the expression of the MYLK gene product based on the physical or functional properties of the MYLK protein in in vitro assay systems (e.g. immunoassays).

The MYLK protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the MYLK gene sequence is identified, the gene product can be isolated and purified using standard methods (e.g. ion exchange, affinity, and gel exclusion chromatography; centrifugation; differential solubility; electrophoresis). Alternatively, native MYLK proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of MYLK or other genes associated with branching morphogenesis. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter MYLK expression may be used in in vivo assays to test for activity of a candidate branching morphogenesis modulating agent, or to further assess the role of MYLK in a branching morphogenesis process such as apoptosis or cell proliferation. Preferably, the altered MYLK expression results in a detectable phenotype, such as decreased or increased levels of cell proliferation, angiogenesis, or apoptosis compared to control animals having normal MYLK expression. The genetically modified animal may additionally have altered branching morphogenesis expression (e.g. branching morphogenesis knockout). Preferred genetically modified animals are mammals such as primates, rodents (preferably mice or rats), among others. Preferred non-mammalian species include zebrafish, C. elegans, and Drosophila. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic Drosophila see Rubin and Spradling, Science (1982) 218:348-53 and U.S. Pat. No. 4,670,388; for transgenic insects see Berghammer A. J. et al. A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous MYLK gene that results in a decrease of MYLK function, preferably such that MYLK expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse MYLK gene is used to construct a homologous recombination vector suitable for altering an endogenous MYLK gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knockin" animal having an alteration in its genome that results in altered expression (e.g., increased (including ectopic) or decreased expression) of the MYLK gene, e.g., by introduction of additional copies of MYLK, or by operatively inserting a regulatory sequence that provides for altered expression of an endogenous copy of the MYLK gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate branching morphogenesis, as animal models of disease and disorders implicating defective branching morphogenesis function, and for in vivo testing of candidate therapeutic agents, such as those identified in screens described below. The candidate therapeutic agents are administered to a genetically modified animal having altered MYLK function and phenotypic changes are compared with appropriate control animals such as genetically modified animals that receive placebo treatment, and/or animals with unaltered MYLK expression that receive candidate therapeutic agent.

In addition to the above-described genetically modified animals having altered MYLK function, animal models having defective branching morphogenesis function (and otherwise normal MYLK function), can be used in the methods of the present invention. For example, a branching morphogenesis knockout mouse can be used to assess, in vivo, the activity of a candidate branching morphogenesis modulating agent identified in one of the in vitro assays described below. Preferably, the candidate branching morphogenesis modulating agent when administered to a model system with cells defective in branching morphogenesis function, produces a detectable phenotypic change in the model system indicating that the branching morphogenesis function is restored, i.e., the cells exhibit normal branching morphogenesis.

Modulating Agents

The invention provides methods to identify agents that interact with and/or modulate the function of MYLK and/or branching morphogenesis. Modulating agents identified by the methods are also part of the invention. Such agents are useful in a variety of diagnostic and therapeutic applications associated with branching morphogenesis, as well as in further analysis of the MYLK protein and its contribution to branching morphogenesis. Accordingly, the invention also provides methods for modulating branching morphogenesis comprising the step of specifically modulating MYLK activity by administering a MYLK-interacting or -modulating agent.

As used herein, a "MYLK-modulating agent" is any agent that modulates MYLK function, for example, an agent that interacts with MYLK to inhibit or enhance MYLK activity or otherwise affect normal MYLK function. MYLK function can be affected at any level, including transcription, protein expression, protein localization, and cellular or extra-cellular activity. In a preferred embodiment, the MYLK-modulating agent specifically modulates the function of the MYLK. The phrases "specific modulating agent", "specifically modulates", etc., are used herein to refer to modulating agents that directly bind to the MYLK polypeptide or nucleic acid, and preferably inhibit, enhance, or otherwise alter, the function of the MYLK. These phrases also encompass modulating agents that alter the interaction of the MYLK with a binding partner, substrate, or cofactor (e.g. by binding to a binding partner of a MYLK, or to a protein/binding partner complex, and altering MYLK function). In a further preferred embodiment, the MYLK-modulating agent is a modulator of branching morphogenesis (e.g. it restores and/or upregulates branching morphogenesis function) and thus is also a branching morphogenesis-modulating agent.

Preferred MYLK-modulating agents include small molecule compounds; MYLK-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the MYLK protein or may be identified by screening compound libraries. Alternative appropriate modulators of this class are natural products, particularly secondary metabolites from organisms such as plants or fungi, which can also be identified by screening compound libraries for MYLK-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with branching morphogenesis. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific MYLK-interacting proteins are useful in a variety of diagnostic and therapeutic applications related to branching morphogenesis and related disorders, as well as in validation assays for other MYLK-modulating agents. In a preferred embodiment, MYLK-interacting proteins affect normal MYLK function, including transcription, protein expression, protein localization, and cellular or extra-cellular activity. In another embodiment, MYLK-interacting proteins are useful in detecting and providing information about the function of MYLK proteins, as is relevant to branching morphogenesis related disorders, such as cancer (e.g., for diagnostic means).

A MYLK-interacting protein may be endogenous, i.e. one that naturally interacts genetically or biochemically with a MYLK, such as a member of the MYLK pathway that modulates MYLK expression, localization, and/or activity. MYLK-modulators include dominant negative forms of MYLK-interacting proteins and of MYLK proteins themselves. Yeast two-hybrid and variant screens offer preferred methods for identifying endogenous MYLK-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928, 868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

An MYLK-interacting protein may be an exogenous protein, such as a MYLK-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). MYLK antibodies are further discussed below.

In preferred embodiments, a MYLK-interacting protein specifically binds a MYLK protein. In alternative preferred embodiments, a MYLK-modulating agent binds a MYLK substrate, binding partner, or cofactor.

Antibodies

In another embodiment, the protein modulator is a MYLK specific antibody agonist or antagonist. The antibodies have therapeutic and diagnostic utilities, and can be used in screening assays to identify MYLK modulators. The antibodies can also be used in dissecting the portions of the MYLK pathway responsible for various cellular responses and in the general processing and maturation of the MYLK.

Antibodies that specifically bind MYLK polypeptides can be generated using known methods. Preferably the antibody is specific to a mammalian ortholog of MYLK polypeptide, and more preferably, to human MYLK. Antibodies may be polyclonal, monoclonal (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Epitopes of MYLK which are particularly antigenic can be selected, for example, by routine screening of MYLK polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence of a MYLK. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of MYLK or substantially purified fragments thereof. If MYLK fragments are used, they preferably comprise at least 10, and more preferably, at least 20 contiguous amino acids of a MYLK protein. In a particular embodiment, MYLK-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of MYLK-specific antibodies is assayed by an appropriate assay such as a solid phase enzyme-linked immunosorbant assay (ELISA) using immobilized corresponding MYLK polypeptides. Other assays, such as radioimmunoassays or fluorescent assays might also be used.

Chimeric antibodies specific to MYLK polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art ((U.S. Pat. Nos. 5,530,101, 5,585,089, 5,693,762, and 6,180,370).

MYLK-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred MYLK-modulating agents comprise nucleic acid molecules, such as antisense oligomers or double stranded RNA (dsRNA), which generally inhibit MYLK activity. Preferred nucleic acid modulators interfere with the function of the MYLK nucleic acid such as DNA replication, transcription, translocation of the MYLK RNA to the site of protein translation, translation of protein from the MYLK RNA, splicing of the MYLK RNA to yield one or more mRNA species, or catalytic activity which may be engaged in or facilitated by the MYLK RNA.

In one embodiment, the antisense oligomer is an oligonucleotide that is sufficiently complementary to a MYLK mRNA to bind to and prevent translation, preferably by binding to the 5' untranslated region. MYLK-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.: 7:187-95; U.S. Pat. No. 5,235,033; and U.S. Pat. No. 5,378,841).

Alternative preferred MYLK nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans, Drosophila*, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No.

6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a MYLK-specific nucleic acid modulator is used in an assay to further elucidate the role of the MYLK in branching morphogenesis, and/or its relationship to other members of the pathway. In another aspect of the invention, a MYLK-specific antisense oligomer is used as a therapeutic agent for treatment of branching morphogenesis-related disease states.

Zebrafish is a particularly useful model for the study of branching morphogenesis using antisense oligomers. For example, PMOs are used to selectively inactive one or more genes in vivo in the Zebrafish embryo. By injecting PMOs into Zebrafish at the 1-16 cell stage candidate targets emerging from the *Drosophila* screens are validated in this vertebrate model system. In another aspect of the invention, PMOs are used to screen the Zebrafish genome for identification of other therapeutic modulators of branching morphogenesis. In a further aspect of the invention, a MYLK-specific antisense oligomer is used as a therapeutic agent for treatment of pathologies associated with branching morphogenesis.

Assay Systems

The invention provides assay systems and screening methods for identifying specific modulators of MYLK activity. As used herein, an "assay system" encompasses all the components required for performing and analyzing results of an assay that detects and/or measures a particular event. In general, primary assays are used to identify or confirm a modulator's specific biochemical or molecular effect with respect to the MYLK nucleic acid or protein. In general, secondary assays further assess the activity of a MYLK modulating agent identified by a primary assay and may confirm that the modulating agent affects MYLK in a manner relevant to branching morphogenesis. In some cases, MYLK modulators will be directly tested in a secondary assay.

In a preferred embodiment, the screening method comprises contacting a suitable assay system comprising a MYLK polypeptide or nucleic acid with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates MYLK activity, and hence branching morphogenesis. The MYLK polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al. Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of MYLK and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when MYLK-interacting proteins are used in screens to identify small molecule modulators, the binding specificity of the interacting protein to the MYLK protein may be assayed by various known methods such as substrate processing (e.g. ability of the candidate MYLK-specific binding agents to function as negative effectors in MYLK-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit MYLK specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a MYLK polypeptide, a fusion protein thereof, or to cells or membranes bearing the polypeptide or fusion protein. The MYLK polypeptide can be full length or a fragment thereof that retains functional MYLK activity. The MYLK polypeptide may be fused to another polypeptide, such as a peptide tag for detection or anchoring, or to another tag. The MYLK polypeptide is preferably human MYLK, or is an ortholog or derivative thereof as described above. In a preferred embodiment, the screening assay detects candidate agent-based modulation of MYLK interaction with a binding target, such as an endogenous or exogenous protein or other substrate that has MYLK-specific binding activity, and can be used to assess normal MYLK gene function.

Suitable assay formats that may be adapted to screen for MYLK modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:7304; Fernandes P B, supra; Hertzberg R P and Pope A J, Curr Opin Chem Biol (2000) 4:445-451).

A variety of suitable assay systems may be used to identify candidate MYLK and branching morphogenesis modulators (e.g. U.S. Pat. No. 6,165,992 (kinase assays); U.S. Pat. Nos. 5,550,019 and 6,133,437 (apoptosis assays); U.S. Pat. Nos. 5,976,782, 6,225,118 and 6,444,434 (angiogenesis assays), among others). Specific preferred assays are described in more detail below.

Protein kinases, key signal transduction proteins that may be either membrane-associated or intracellular, catalyze the transfer of gamma phosphate from adenosine triphosphate (ATP) to a serine, threonine or tyrosine residue in a protein substrate. Radioassays, which monitor the transfer from [gamma-$^{32}$P or -$^{33}$P] ATP, are frequently used to assay kinase activity. For instance, a scintillation assay for p56 (lck) kinase activity monitors the transfer of the gamma phosphate from [gamma-$^{33}$P] ATP to a biotinylated peptide substrate. The substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand. Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA® (Sadick M D, Dev Biol Stand (1999) 97:121-133). Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64).

Apoptosis assays. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al. 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available APO-ONE™ Homogeneous Caspase-3/7 assay from Promega, cat#67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat# 1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumulation in the cytoplasm. Nucleosomes are not present in the cytoplasmic fraction of cells that are not undergoing apoptosis. An apoptosis assay system may comprise a cell that expresses a MYLK, and that optionally has defective branching morphogenesis function. A test agent can be added to the apoptosis assay system and changes in induction of apoptosis, relative to controls where no test agent is added, identify candidate branching morphogenesis modulating agents. In some embodiments of the invention, an apoptosis assay may be used as a secondary assay to test a candidate branching morphogenesis modulating agents that is initially identified using a cell-free assay system. An apoptosis assay may also be used to test whether MYLK function plays a direct role in apoptosis. For example, an apoptosis assay may be performed on cells that over- or under-express MYLK relative to wild type cells. Differences in apoptotic response compared to wild type cells suggests that the MYLK plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CELLTITER96® Aqueous Non-Radioactive Cell Proliferation Assay (Cat.# G5421).

Cell proliferation may also be assayed by colony formation in soft agar (Sambrook et al., Molecular Cloning, Cold Spring Harbor (1989)). For example, cells transformed with MYLK are seeded in soft agar plates, and colonies are measured and counted after two weeks incubation.

Cell proliferation may also be assayed by measuring ATP levels as indicator of metabolically active cells. Such assays are commercially available, for example Cell TITER-GLO™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a MYLK may be stained with propidium iodide and evaluated in a flow cytometer (available from Becton Dickinson), which indicates accumulation of cells in different stages of the cell cycle.

Accordingly, a cell proliferation or cell cycle assay system may comprise a cell that expresses a MYLK, and that optionally has defective branching morphogenesis function. A test agent can be added to the assay system and changes in cell proliferation or cell cycle relative to controls where no test agent is added, identify candidate branching morphogenesis modulating agents. In some embodiments of the invention, the cell proliferation or cell cycle assay may be used as a secondary assay to test a candidate branching morphogenesis modulating agents that is initially identified using another assay system such as a cell-free assay system. A cell proliferation assay may also be used to test whether MYLK function plays a direct role in cell proliferation or cell cycle. For example, a cell proliferation or cell cycle assay may be performed on cells that over- or under-express MYLK relative to wild type cells. Differences in proliferation or cell cycle compared to wild type cells suggests that the MYLK plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on MATRIGEL® (Becton Dickinson). Accordingly, an angiogenesis assay system may comprise a cell that expresses a MYLK, and that optionally has defective branching morphogenesis function. A test agent can be added to the angiogenesis assay system and changes in angiogenesis, relative to controls where no test agent is added, identify candidate branching morphogenesis modulating agents. In some embodiments of the invention, the angiogenesis assay may be used as a secondary assay to test a candidate branching morphogenesis modulating agent that is initially identified using another assay system. An angiogenesis assay may also be used to test whether MYLK function plays a direct role in cell proliferation. For example, an angiogenesis assay may be performed on cells that over- or under-express MYLK relative to wild type cells. Differences in angiogenesis compared to wild type cells suggest that the MYLK plays a direct role in angiogenesis. U.S. Pat. Nos. 5,976,782, 6,225,118 and 6,444,434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glycolytic enzymes and VEGF. Induction of such genes by hypoxic conditions may be assayed by growing cells transfected with MYLK in hypoxic conditions (such as with 0.1% O2, 5% CO2, and balance N2, generated in a NAPCO® 7001 incubator (Precision Scientific)) and normoxic conditions, followed by assessment of gene activity or expression by TAQMAN®. For example, a hypoxic induction assay system may comprise a cell that expresses a MYLK, and that optionally has defective branching morphogenesis function. A test agent can be added to the hypoxic induction assay system and changes in hypoxic response relative to controls where no test agent is added, identify candidate branching morphogenesis modulating agents. In some embodiments of the invention, the hypoxic induction assay may be used as a secondary assay to test a candidate branching morphogenesis modulating agent that is initially identified using another assay system. A hypoxic induction assay may also be used to test whether MYLK function plays a direct role in the hypoxic response. For example, a hypoxic induction assay may be performed on cells that over- or under-express MYLK relative to wild type cells. Differences in hypoxic response compared to wild type cells suggest that the MYLK plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Tubulogenesis. Tubulogenesis assays monitor the ability of cultured cells, generally endothelial cells, to form tubular structures on a matrix substrate, which generally simulates the environment of the extracellular matrix. Exemplary substrates include MATRIGEL™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. Serum represents an undefined source of growth factors. In a preferred embodiment, the assay is performed with cells cultured in serum free medium, in order to control which process or pathway a candidate agent modulates. Moreover, we have found that different target genes respond differently to stimulation with different pro-angiogenic agents, including inflammatory angiogenic factors such as TNF-alpa. Thus, in a further preferred embodiment, a tubulogenesis assay system comprises testing a MYLK's response to a variety of factors, such as FGF, VEGF, phorbol myristate acetate (PMA), TNF-alpha, ephrin, etc.

Cell Migration. An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific, South San Francisco, Calif.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. As described above, a preferred assay system for migration/invasion assays comprises testing a MYLK's response to a variety of pro-angiogenic factors, including tumor angiogenic and inflammatory angiogenic agents, and culturing the cells in serum free medium.

Sprouting assay. A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 µl of methocel-collagen solution and pipetted into individual wells of a 24 well plate to allow collagen gel polymerization. Test agents are added after 30 min by pipetting 100 µl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the MYLK protein. Methods for testing antibody affinity and specificity are well known in the art (Harlow and Lane, 1988, 1999, supra). The enzyme-linked immunosorbant assay (ELISA®) is a preferred method for detecting MYLK-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance MYLK gene expression, preferably mRNA expression. In general, expression analysis comprises comparing MYLK expression in like populations of cells (e.g., two pools of cells that endogenously or recombinantly express MYLK) in the presence and absence of the nucleic acid modulator. Methods for analyzing mRNA and protein expression are well known in the art. For instance, Northern blotting, slot blotting, ribonuclease protection, quantitative RT-PCR (e.g., using the TAQMAN®, PE APPLIED BIOSYSTEMS® ), or microarray analysis may be used to confirm that MYLK mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the MYLK protein or specific peptides. A variety of means including Western blotting, ELISA®, or in situ detection, are available (Harlow E and Lane D, 1988 and 1999, supra).

In some cases, screening assays described for small molecule modulators, particularly in assay systems that involve MYLK mRNA expression, may also be used to test nucleic acid modulators.

Secondary Assays

Secondary assays may be used to further assess the activity of MYLK-modulating agent identified by any of the above methods to confirm that the modulating agent affects MYLK in a manner relevant to branching morphogenesis. As used herein, MYLK-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with MYLK.

Secondary assays generally compare like populations of cells or animals (e.g., two pools of cells or animals that endogenously or recombinantly express MYLK) in the presence and absence of the candidate modulator. In general, such assays test whether treatment of cells or animals with a candidate MYLK-modulating agent results in changes in branching morphogenesis in comparison to untreated (or mock- or placebo-treated) cells or animals. Certain assays use "sensitized genetic backgrounds", which, as used herein, describe cells or animals engineered for altered expression of genes in the branching morphogenesis or interacting pathways.

Cell-Based Assays

Cell based assays may use a variety of mammalian cell types. Preferred cells are capable of branching morphogenesis processes and are generally endothelial cells. Exemplary cells include human umbilical vein endothelial cells (HUVECs), human renal microvascular endothelial cells (HRMECs), human dermal microvascular endothelial cells (HDMECs), human uterine microvascular endothelial cells, human lung microvascular endothelial cells, human coronary artery endothelial cells, and immortalized microvascular cells, among others. Cell based assays may rely on the endogenous expression of MYLK and/or other genes, such as those involved in branching morphogenesis, or may involve recombinant expression of these genes. Candidate modulators are typically added to the cell media but may also be injected into cells or delivered by any other efficacious means.

Cell-based assays may detect a variety of events associated with branching morphogenesis and angiogenesis, including cell proliferation, apoptosis, cell migration, tube formation, sprouting and hypoxic induction, as described above.

Animal Assays

A variety of non-human animal models of branching morphogenesis, including angiogenesis, and related pathologies may be used to test candidate MYLK modulators. Animal assays may rely on the endogenous expression of MYLK and/or other genes, such as those involved in branching morphogenesis, or may involve engineered expression of these genes. In some cases, MYLK expression or MYLK protein may be restricted to a particular implanted tissue or matrix. Animal assays generally require systemic delivery of a candidate modulator, such as by oral administration, injection (intravenous, subcutaneous, intraperitoneous), bolus administration, etc.

In a preferred embodiment, branching morphogenesis activity is assessed by monitoring neovascularization and angiogenesis. Animal models with defective and normal branching morphogenesis are used to test the candidate modulator's effect on MYLK in MATRIGEL® assays. MATRIGEL® is an extract of basement membrane proteins, and is composed primarily of laminin, collagen IV, and heparin sulfate proteoglycan. It is provided as a sterile liquid at 4° C., but rapidly forms a solid gel at 37° C. Liquid MATRIGEL® is mixed with various angiogenic agents, such as bFGF and VEGF, or with human tumor cells which overexpress the MYLK. The mixture is then injected subcutaneously (SC) into female athymic nude mice (Taconic, Germantown, N.Y.) to support an intense vascular response. Mice with MATRIGEL® pellets may be dosed via oral (PO), intraperitoneal (IP), or intravenous (IV) routes with the candidate modulator. Mice are euthanized 5-12 days post-injection, and the MATRIGEL® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on MYLK is assessed via tumorigenicity assays. In one example, a xenograft comprising human cells from a pre-existing tumor or a tumor cell line known to be angiogenic is used; exemplary cell lines include A431, Colo205, MDA-MB-435, A673, A375, Calu-6, MDA-MB-231, 460, SF763T, or SKOV3tp5. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the MYLK endogenously are injected in the flank, $1\times10^5$ to $1\times10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line known to be angiogenic. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc. Other assays specific to angiogenesis, as are known in the art and described herein, may also be used.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific MYLK-modulating agents are useful in a variety of diagnostic and therapeutic applications where disease or disease prognosis is related to defects in branching morphogenesis, such as angiogenic, apoptotic, or cell proliferation disorders. Accordingly, the invention also provides methods for modulating branching morphogenesis in a cell, preferably a cell pre-determined to have defective or impaired branching morphogenesis function (e.g. due to overexpression, underexpression, or misexpression of branching morphogenesis, or due to gene mutations), comprising the step of administering an agent to the cell that specifically modulates MYLK activity. Preferably, the modulating agent produces a detectable phenotypic change in the cell indicating that the branching morphogenesis function is restored. The phrase "function is restored", and equivalents, as used herein, means that the desired phenotype is achieved, or is brought closer to normal compared to untreated cells. For example, with restored branching morphogenesis function, cell proliferation and/or progression through cell cycle may normalize, or be brought closer to normal relative to untreated cells. The invention also provides methods for treating disorders or disease associated with impaired branching morphogenesis function by administering a therapeutically effective amount of a MYLK-modulating agent that modulates branching morphogenesis. The invention further provides methods for modulating MYLK function in a cell, preferably a cell pre-determined to have defective or impaired MYLK function, by administering a MYLK-modulating agent. Additionally, the invention provides a method for treating disorders or disease associated with impaired MYLK function by administering a therapeutically effective amount of a MYLK-modulating agent.

The discovery that MYLK is implicated in branching morphogenesis provides for a variety of methods that can be employed for the diagnostic and prognostic evaluation of diseases and disorders involving defects in branching morphogenesis and for the identification of subjects having a predisposition to such diseases and disorders.

Various expression analysis methods can be used to diagnose whether MYLK expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective branching morphogenesis signaling that express a MYLK, are identified as amenable to treatment with a MYLK modulating agent. In a preferred application, the branching morphogenesis defective tissue overexpresses a MYLK relative to normal tissue. For example, a Northern blot analysis of mRNA from tumor and normal cell lines, or from tumor and matching normal tissue samples from the same patient, using full or partial MYLK cDNA sequences as probes, can determine whether particular tumors express or overexpress MYLK. Alternatively, the TAQMAN® is used for quantitative RT-PCR analysis of MYLK expression in cell lines, normal tissues and tumor samples (PE APPLIED BIOSYSTEMS®).

Various other diagnostic methods may be performed, for example, utilizing reagents such as the MYLK oligonucleotides, and antibodies directed against a MYLK, as described above for: (1) the detection of the presence of MYLK gene mutations, or the detection of either over- or under-expression of MYLK mRNA relative to the non-disorder state; (2) the detection of either an over- or an under-abundance of MYLK gene product relative to the non-disorder state; and (3) the detection of perturbations or abnormalities in the signal transduction pathway mediated by MYLK.

Kits for detecting expression of MYLK in various samples, comprising at least one antibody specific to MYLK, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in MYLK expression, the method comprising: a) obtaining a biological sample from the patient; b) contacting the sample with a probe for MYLK expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. Zebrafish Screen

Wild type, one-cell stage embryos from the Tübingen strain were treated with antisense morpholino oligonucleotide (PMOS) that targeted the 5'UTR and/or start codon of predicted zebrafish genes. PMOs were dissolved at a concentration of 3 mg/mL in injection buffer (0.4 mM $MgSO_4$, 0.6 mM $CaCl_2$, 0.7 mM KCl, 58 mM NaCl, 25 mM Hepes [pH 7.6]); a total of 1.5 nL (=4.5 ng) was injected into zebrafish embryos at the 1-cell stage.

Larvae were fixed at 4 days post fertilization (dpf) in 4% para-formaldehyde in phosphate-buffered saline (PBS) for 30 minutes. Fixed larvae were dehydrated in methanol and stored over night at $-20°$ C. After permeabilization in acetone (30 minutes at $-20°$ C.), embryos were washed in PBS and incubated in the staining buffer (100 mM Tris-HCl [pH 9.5], 50 mM $MgCl_2$, 100 mM NaCl, 0.1% Tween-20) for 45 minutes. Staining reaction was started by adding 2.25 µl nitro blue tetrazolium (NBT, Sigma) and 1.75 µl 5-bromo-chloro-3-indolyl phosphate (BCIP, Sigma) per ml of staining buffer (stock solutions: 75 mg/ml NBT in 70% N,N-dimethylformamide, 50 mg/ml BCIP in N,N-dimethylformamide).

The fixed specimens were scanned for changes in blood vessel formation, in particular, for any pro-angiogenic, anti-angiogenic, vasculogenic or vessel patterning phenotypes, among others. Other phenotypic changes resulting from the PMO treatment were also noted. Hits were "Confirmed" when the phenotype was seen for $2^{nd}$ time in an independent injection of the PMO. Hits were "Characterized" when phenotype was seen for a $3^{rd}$ time by angiography, to visualize the vascular anatomy. DR-MYLK was identified as a modifier, as its antisense knockdown led to reduced intersegmental and pectoral fin vessel formation. Orthologs of the modifiers are referred to herein as MYLK.

BLAST analysis (Altschul et al., supra) was employed to identify orthologs of *Drosophila* modifiers. For example, representative sequences from MYLK, GI#16950611 (SEQ ID NO: 11), shares 43% amino acid identity with the zebrafish DR-MYLK.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and dust (Remm M, and Sonnhammer E. Classification of transmembrane protein families in the *Caenorhabditis elegans* genome and identification of human orthologs. Genome Res. 2000 November; 10(11):1679-89) programs. For example, the kinase domain (PFAM 00069) of MYLK from GI#16950611 (SEQ ID NO: 11) is located at approximately amino acid residues 1464 to 1719. Likewise, the Immunoglobulin domain (PF00047) of the same protein is located at approximately amino acid residues 47 to 108, 175 to 235, 428 to 489, 528 to 585, 637 to 697, 735 to 796, 1112 to 1172, 1252 to 1312, and 1823 to 1884.

II. Zebrafish "Negative" & "Positive" Secondary Assays for Morpholino (PMO) Screen Hits Zebrafish "Negative" secondary assays are used to determine whether the effects seen on the vasculature with the morpholino knockdown is a primary effect on the vasculature vs. a secondary effect caused by a general patterning defect. Zebrafish "Positive" secondary assays provide pathway and/or mechanistic information about the gene target as well as cell and tissue specificity of its activity.

Negative assay #1—Patterning vs. vascular defects. Whole mount stains are done with muscle-specific antibody mAb MF20 (acto-myosin) to evaluate whether there is a general patterning defect caused by the gene knockdown.

Negative assay #2—Neuronal vs. vascular defects. Whole mount stains with a neuronal-specific antibody (anti-acetylated tubulin) to evaluate whether there is a underlying neuronal patterning defect that may cause a secondary vascular phenotype.

Negative assay #3—Tissue dystrophic or necrotic vs. vascular defects. Live observation of morphology under Nomarski optics (at day 1-4 of development following PMO injection) to evaluate the extent of tissue apoptosis/necrosis induced by gene knockdown.

Negative assay #4—Vascular or Hematopoietic Marker Expression (in situ hybridization). In situ hybridization w/fli1 gene, which stains developing vessels, is done at day 2 of development to evaluate whether the phenotype observed at day 4 results from a vascular development defect vs. vascular maintenance defect.

Positive assay #5: Anti-Angiogenesis pathway interactions with VEGF-Receptor (KDR) and with Target gene PMOs. Target gene PMO with PMO to knockdown the KDR (VEGFR2) gene are co-injected to evaluate whether the target functions in the VEGF pathway.

III. High-Throughput In Vitro Fluorescence Polarization Assay

Fluorescently-labeled MYLK peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of MYLK activity.

IV. High-Throughput In Vitro Binding Assay.

$^{33}$P-labeled MYLK peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate branching morphogenesis modulating agents.

V. Immunoprecipitations and Immunoblotting

For coprecipitation of transfected proteins, $3 \times 10^6$ appropriate recombinant cells containing the MYLK proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM—glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

VI. Kinase Assay

A purified or partially purified MYLK is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 mM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation ($Mg^{2+}$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

V. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, UC Davis, CLONTECH™, STRATAGENE®, Ardais, Genome Collaborative, and AMBION®.

TAQMAN® analysis was used to assess expression levels of the disclosed genes in various samples.

RNA was extracted from each tissue sample using QIAGEN™ (Valencia, Calif.) RNEASY® kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of APPLIED BIOSYSTEMS® (Foster City, Calif.).

Primers for expression analysis using TAQMAN® assay (APPLIED BIOSYSTEMS®, Foster City, Calif.) were prepared according to the TAQMAN® protocols, and the following criteria: a) primer pairs were designed to span introns to eliminate genomic contamination, and b) each primer pair produced only one product. Expression analysis was performed using a 7900HT instrument.

TAQMAN® reactions were carried out following manufacturer's protocols, in 25 μl total volume for 96-well plates and 10 μl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average (all normal samples)>2× STDEV (all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| Gene Name | MYLK |
|---|---|
| SEQ ID NO | 2 |
| Breast | 14% |
| # of Pairs | 36. |
| Colon | 12% |
| # of Pairs | 41 |
| Head And Neck | 38% |
| # of Pairs | 13 |
| Kidney | 4% |
| # of Pairs | 23 |
| Liver | 0% |
| # of Pairs | 8 |
| Lung | 2% |
| # of Pairs | 42 |
| Lymphoma | 0% |
| # of Pairs | 4 |
| Ovary | 5% |
| # of Pairs | 19 |
| Pancreas | 69% |
| # of Pairs | 13 |
| Prostate | 4% |
| # of Pairs | 24 |
| Skin | 14% |
| # of Pairs | 7 |
| Stomach | 27% |
| # of Pairs | 11 |
| Testis | 0% |
| # of Pairs | 8 |

TABLE 1-continued

| Thyroid Gland | 7% |
|---|---|
| # of Pairs | 14 |
| Uterus | 14% |
| # of Pairs | 22 |

VI. Proliferation Assay

Human umbilical endothelial cells (HMVEC) are maintained at 37° C. in flasks or plates coated with 1.5% porcine skin gelatin (300 bloom, Sigma) in Growth medium (Clonetics Corp.) supplemented with 10-20% fetal bovine serum (FBS, Hyclone). Cells are grown to confluency and used up to the seventh passage. Stimulation medium consists of 50% Sigma 99 media and 50% RPMI 1640 with L-glutamine and additional supplementation with 10 Ag/ml insulin-transferrin-selenium (Gibco BRL) and 10% FBS. Cell growth is stimulated by incubation in Stimulation medium supplemented with 20 ng/ml of VEGF. Cell culture assays are carried out in triplicate. Cells are transfected with a mixture of 10 μg of pSV7d expression vectors carrying the MYLK or the MYLK coding sequences and 1 μg of pSV2 expression vector carrying the neo resistance gene with the Lipofectin reagent (Life Technologies, Inc.). Stable integrants are selected using 500 μg/ml G418; cloning was carried out by colony isolation using a Pasteur pipette. Transformants are screened by their ability to specifically bind iodinated VEGF. Proliferation assays are performed on growth-arrested cells seeded in 24-well cluster plates. The cell monolayers are incubated in serum-free medium with the modulators and 1 μCi of [3H] thymidine (47 Ci/mmol) for 4 h. The insoluble material is precipitated for 10 min with 10% trichloroacetic acid, neutralized, and dissolved in 0.2 M NaOH, and the radioactivity is counted in a scintillation counter.

VII. MYLK Functional Analysis

The role of MLCK in branching morphogenesis was examined using cell adhesion, migration, extravasation and vascular permeability assays in human cell cultures.

T-cell adhesion is mediated by beta2 integrin/ICAM-1 interaction. Cell adhesion to ICAM-1 was assayed, as explained in the "cell adhesion assay" section above, by coating plates with 2 μg/ml of recombinant ICAM-1. THP-1 cells (a monocyte cell line) were assayed for their ability to adhere to ICAM-1 coated plates. LFA-1 (beta2 integrin) blocking antibodies inhibited THP-1 cells from adhering to ICAM-1, as did a MYLK inhibitor ML-7. ML-7 inhibited the adhesion in a dose-dependent manner and independent of cell stimulus (e.g., PMA or MCP-1). THP-1 adhesion to ICAM-1 induced Myosin Regulatory Light Chain (MLC) phosphorylation (the main substrate for MYLK), and ML-7 treatment inhibited ICAM-1 induced MLC phosphorylation. Expression of a dominant negative form of MYLK (MYLK-DN) in THP-1 cells similarly reduced cell adhesion to ICAM-1. An activated form of MYLK (MYLK-AC) expressed in monocyte cells enhanced adhesion to ICAM-1. Cell migration assays, as described above, were employed to investigate the ability of THP-1 cells for trans-endothelial migration (migration of THP-1 cells through an endothelial cell monolayer). Human vascular endothelial cells (HUVEC) were grown to a monolayer in the upper chamber of a Boyden chamber. THP-1 cells added to the upper chamber were assayed for their ability to traverse the endothelial monolayer and the filter membrane support to the lower chamber in response to stimuli (MCP-1). ML-7, by inhibiting MYLK, also inhibited the trans-endothelial migration of THP-1 cells in a dose-dependent manner. In addition, expression of MYLK-DN in HUVEC cells reduced THP-1 trans-endothelial migration induced by TNFalpha.

What is claimed is:

1. A method for diagnosing cancer in a subject comprising:
   (a) obtaining a biological sample from the subject;
   (b) determining the level of expression of Myosin Light Chain Kinase (MYLK) in the biological sample of step (a);
   (c) comparing the level of expression of MYLK in the biological sample of step (b) with the level of expression of MYLK in a control sample; and
   (d) determining an elevated level of MYLK expression in the biological sample compared with the control sample, wherein said elevated level provides a diagnosis of cancer, wherein the cancer is selected from stomach and head and neck cancer.

2. The method of claim 1, wherein the control sample is a non-cancerous sample derived from tissue that matches that of the biological sample of the subject.

3. The method of claim 1, wherein the MYLK comprises SEQ ID NO: 2 or an encoded polypeptide thereof.

4. The method of claim 1, wherein the level of MYLK expression in the biological sample is at least 2-fold higher than the level of expression in the control sample.

5. The method of claim 1, wherein the level of MYLK expression is determined using an MYLK nucleic acid or antibody.

* * * * *

SEQUENCE LISTING

<160> NUMBER OF SEQ ID NOS: 11

<210> SEQ ID NO 1
<211> LENGTH: 3426
<212> TYPE: DNA
<213> ORGANISM: Homo sapiens

<400> SEQUENCE: 1

```
ttcaggaacc gggttggcga atcgagttgc caggtgtcac tgatgctaca gaacagctct      60
gccagcagcc ttccacgggg gagggagcct gccagctgcg aggacctctg tggtggagga     120
gttggtgctg atggtggtgg tagtgaccgc tatgggtccc tgaggcctgg ctggccagca     180
agagggcagg gttggctaga ggaggaagac ggcgaggacg tgcgaggggt gctgaagagg     240
cgcgtggaga cgaggcagcc aactgaggag gcgatccccg agcaggaggt ggagcagctg     300
gacttccgag acctcctggg gaagaaggtg agtacaaaga ccctatcgga agacgacctg     360
aaggagatcc cagccgagca gatggatttc cgtgccaacc tgcagcggca agtgaagcca     420
aagactgtgt ctgaggaaga gaggaaggtg cacagccccc agcaggtcga ttttcgctct     480
gtcctggcca agaaggggac ttccaagacc cccgtgcctg agaaggtgcc accgccaaaa     540
cctgccaccc cggattttcg ctcagtgctg ggtggcaaga gaaattacc agcagagaat     600
ggcagcagca gtgccgagac cctgaatgcc aaggcagtgg agttccaa gcccctgagc     660
aatgcacagc cttcagggcc cttgaaaccc gtgggcaacg ccaagcctgc tgagaccctg     720
aagccaatgg gcaacgccaa gcctgccgag accctgaagc ccatgggcaa tgccaagcct     780
gatgagaacc tgaaatccgc tagcaaagaa gaactcaaga agacgttaa gaatgatgtg     840
aactgcaaga gaggccatgc agggaccaca gataatgaaa agagatcaga gagccagggg     900
acagccccag ccttcaagca gaagctgcaa gatgttcatg tggcagaggg caagaagctg     960
ctgctccagt gccaggtgtc ttctgacccc ccagccacca tcatctggac gctgaatgga    1020
aagaccctca agaccaccaa gttcatcatc ctctcccagg aaggctcact ctgctccgtc    1080
tccatcgaga aggcactgcc tgaggacaga ggcttataca gtgtgtagc caagaatgac    1140
gctggccagg cggagtgctc ctgccaagtc accgtggatg atgctccagc cagtgagaac    1200
accaaggccc cagagatgaa atcccggagg cccaagagct ctcttcctcc cgtgctagga    1260
actgagagtg atgcgactgt gaaaaagaaa cctgccccca agacacctcc gaaggcagca    1320
atgccccctc agatcatcca gttccctgag gaccagaagg tacgcgcagg agagtcagtg    1380
gagctgtttg gcaaagtgac aggcactcag cccatcacct gtacctggat gaagttccga    1440
aagcagatcc aggaaagcga gcacatgaag gtggagaaca gcgagaatgg cagcaagctc    1500
accatcctgg ccgcgcgcca ggagcactgc ggctgctaca cactgctggt ggagaacaag    1560
ctgggcagca gcaggcccca ggtcaacctc actgtcgtgg ataagccaga ccccccagct    1620
ggcacacctt gtgcctctga cattcggagc tcctcactga ccctgtcctg gtatggctcc    1680
tcatatgatg gggcagtgc tgtacagtcc tacagcatcg agatctggga ctcagccaac    1740
aagacgtgga aggaactagc cacatgccgc agcacctctt tcaacgtcca ggacctgctg    1800
cctgaccacg aatataagtt ccgtgtacgt gcaatcaacg tgtatggaac cagtgagcca    1860
agccaggagt ctgaactcac aacggtagga gagaaacctg aagagccgaa ggatgaagtg    1920
gaggtgtcag acgatgatga aggagcccc gaggttgatt ccggacagt gacaatcaat    1980
actgaacaaa agtatctga cttctacgac attgaggaga gattaggatc tgggaaattt    2040
```

-continued

| | |
|---|---|
| ggacaggtct ttcgacttgt agaaaagaaa actcgaaaag tctgggcagg gaagttcttc | 2100 |
| aaggcatatt cagcaaaaga gaaagagaat atccggcagg agattagcat catgaactgc | 2160 |
| ctccaccacc ctaagctggt ccagtgtgtg gatgcctttg aagaaaaggc caacatcgtc | 2220 |
| atggtcctgg agatcgtgtc aggaggggag ctgtttgagc gcatcattga cgaggacttt | 2280 |
| gagctgacgg agcgtgagtg catcaagtac atgcggcaga tctcggaggg agtggagtac | 2340 |
| atccacaagc agggcatcgt gcacctggac ctcaagccgg agaacatcat gtgtgtcaac | 2400 |
| aagacgggca ccaggatcaa gctcatcgac tttggtctgg ccaggaggct ggagaacgcg | 2460 |
| gggtctctga aggtcctctt tggcacccca gaatttgtgg ctcctgaagt gatcaactat | 2520 |
| gagcccatcg gctacgccac agacatgtgg agcatcgggg tcatctgcta catcctagtc | 2580 |
| agtggccttt ccccttcat gggagacaac gataacgaaa ccttggccaa cgttacctca | 2640 |
| gccacctggg acttcgacga cgaggcattc gatgagatct ccgacgatgc caaggatttc | 2700 |
| atcagcaatc tgctgaagaa agatatgaaa accgcctgg actgcacgca gtgccttcag | 2760 |
| catccatggc taatgaaaga taccaagaac atggaggcca agaaactctc caaggaccgg | 2820 |
| atgaagaagt acatggcaag aaggaaatgg cagaaaacgg gcaatgctgt gagagccatt | 2880 |
| ggaagactgt cctctatggc aatgatctca gggctcagtg caggaaaatc ctcaacaggg | 2940 |
| tcaccaacca gcccgctcaa tgcagaaaaa ctagaatctg aagatgtgtc ccaagctttc | 3000 |
| cttgaggctg ttgctgagga aaagcctcat gtaaaaccct atttctctaa gaccattcgc | 3060 |
| gatttagaag ttgtggaggg aagtgctgct agatttgact gcaagattga aggataccca | 3120 |
| gaccccgagg ttgtctggtt caaagatgac cagtcaatca gggagtcccg ccacttccag | 3180 |
| atagactacg atgaggacgg gaactgctct ttaattatta gtgatgtttg cggggatgac | 3240 |
| gatgccaagt acacctgcaa ggctgtcaac agtcttggag aagccacctg cacagcagag | 3300 |
| ctcattgtgg aaacgatgga ggaaggtgaa ggggaagggg aagaggaaga agagtgaaac | 3360 |
| aaagccagag aaaagcagtt tctaagtcat attaaaagga ctatttctct aaaactcaaa | 3420 |
| aaaaaa | 3426 |

<210> SEQ ID NO 2
<211> LENGTH: 5925
<212> TYPE: DNA
<213> ORGANISM: Homo sapiens

<400> SEQUENCE: 2

| | |
|---|---|
| ccggctgcct ctgctgcagt tcagagcaac ttcaggagct tcccagccga gagcttcagg | 60 |
| acgcctttcc tgtcccactg gcccagttgc cacaacaaac aacagagaag acggtgacca | 120 |
| tgggggatgt gaagctggtt gcctcgtcac acatttccaa aacctccctc agtgtggatc | 180 |
| cctcaagagt tgactccatg cccctgacag aggcccctgc tttcattttg cccctcgga | 240 |
| acctctgcat caaagaagga gccaccgcca gttcgaagg gcgggtccgg ggttacccag | 300 |
| agccccaggt gacatggcac agaaacgggc aacccatcac cagcggggc cgcttcctgc | 360 |
| tggattgcgg catccggggg actttcagcc ttgtgattca tgctgtccat gaggaggaca | 420 |
| ggggaaagta tacctgtgaa gccaccaatg gcagtggtgc tcgccaggtg acagtggagt | 480 |
| tgacagtaga aggaagtttt gcgaagcagc ttggtcagcc tgttgtttcc aaaaccttag | 540 |
| gggatagatt ttcagcttca gcagtggaga cccgtcctag catctggggg gagtgccac | 600 |
| caaagtttgc taccaagctg ggccgagttg tggtcaaaga aggacagatg ggacgattct | 660 |
| cctgcaagat cactggccgg ccccaaccgc aggtcacctg gctcaaggga aatgttccac | 720 |

```
tgcagccgag tgcccgtgtg tctgtgtctg agaagaacgg catgcaggtt ctggaaatcc      780
atggagtcaa ccaagatgac gtgggagtgt acacgtgcct ggtggtgaac gggtcgggga      840
aggcctcgat gtcagctgaa ctttccatcc aaggtttgga cagtgccaat aggtcatttg      900
tgagagaaac aaaagccacc aattcagatg tcaggaaaga ggtgaccaat gtaatctcaa      960
aggagtcgaa gctggacagt ctggaggctg agccaaaaag caagaactgc tccagccccc     1020
agagaggtgg ctccccaccc tgggctgcaa acagccagcc tcagccccca agggagtcca     1080
agctggagtc atgcaaggac tcgcccagaa cggccccgca gaccccggtc cttcagaaga     1140
cttccagctc catcaccctg caggccgcaa gagttcagcc ggaaccaaga gcaccaggcc     1200
tgggggtcct atcaccttct ggagaagaga ggaagaggcc agctcctccc cgtccagcca     1260
ccttccccac caggcagcct ggcctgggga gccaagatgt tgtgagcaag gctgctaaca     1320
ggagaatccc catggagggc cagagggatt cagcattccc caaatttgag agcaagcccc     1380
aaagccagga ggtcaaggaa aatcaaactg tcaagttcag atgtgaagtt ccgggattc      1440 caaagcctga agtggcctgg ttcctggaag gcaccccgt gaggagacag gaaggcagca     1500
ttgaggttta tgaagatgct ggctcccatt acctctgcct gctgaaagcc cggaccaggg     1560
acagtgggac atacagctgc actgcttcca cgcccaagg ccaggtgtcc tgtagctgga     1620
ccctccaagt ggaaaggctt gccgtgatgg aggtggcccc ctccttctcc agtgtcctga     1680
aggactgcgc tgttattgag ggccaggatt ttgtgctgca gtgctccgta cgggggaccc     1740
cagtgccccg gatcacttgg ctgctgaatg ggcagcccat ccagtacgct cgctccacct     1800
gcgaggccgg cgtggctgag ctccacatcc aggatgccct gccggaggac catggcacct     1860
acacctgcct agctgagaat gccttggggc aggtgtcctg cagcgcctgg gtcaccgtcc     1920
atgaaaagaa gagtagcagg aagagtgagt accttctgcc tgtggctccc agcaagccca     1980
ctgcacccat cttcctgcag ggcctctctg atctcaaagt catggatgga agccaggtca     2040
ctatgactgt ccaagtgtca gggaatccac cccctgaagt catctggctg cacaatggga     2100
atgagatcca agagtcagag gacttccact ttgaacagag aggaactcag cacagccttt     2160
ggatccagga agtgttcccg gaggacacgg gcacgtacac ctgcgaggcc tggaacagcg     2220
ctggagaggt ccgcacccag gccgtgctca cggtacaaga gcctcacgat ggcacccagc     2280
cctggttcat cagtaagcct cgctcagtga cagcctccct gggccagagt gtcctcatct     2340
cctgcgccat agctggtgac ccctttccta ccgtgcactg gctcagagat ggcaaagccc     2400
tctgcaaaga cactggccac ttcgaggtgc ttcagaatga ggacgtgttc acctggttc      2460 taaagaaggt gcagccctgg catgccggcc agtatgagat cctgctcaag aaccgggttg     2520
gcgaatgcag ttgccaggtg tcactgatgc tacagaacag ctctgccaga gcccttccac     2580
gggggaggga gcctgccagc tgcgaggacc tctgtggtgg aggagttggt gctgatggtg     2640
gtggtagtga ccgctatggg tccctgaggc ctggctggcc agcaagaggg cagggttggc     2700
tagaggagga agacggcgag gacgtgcgag gggtgctgaa gaggcgcgtg gagacgaggc     2760
agcacactga ggaggcgatc cgccagcagg aggtggagca gctggacttc cgagacctcc     2820
tggggaagaa ggtgagtaca aagaccctat cggaagacga cctgaaggag atcccagccg     2880
agcagatgga tttccgtgcc aacctgcagc ggcaagtgaa gccaaagact gtgtctgagg     2940
aagagaggaa ggtgcacagc ccccagcagg tcgattttcg ctctgtcctg gccaagaagg     3000
ggacttccaa gaccccgtg cctgagaagg tgccaccgcc aaaacctgcc accccggatt      3060
ttcgctcagt gctgggtggc aagaagaaat accagcagag gaatgcagc agcagtgccg      3120
```

```
agaccctgaa tgccaaggca gtggagagtt ccaagcccct gagcaatgca cagccttcag    3180
ggcccttgaa acccgtgggc aacgccaagc ctgctgagac cctgaagcca atgggcaacg    3240
ccaagcctgc cgagaccctg aagcccatgg gcaatgccaa gcctgatgag aacctgaaat    3300
ccgctagcaa agaagaactc aagaaagacg ttaagaatga tgtgaactgc aagagaggcc    3360
atgcagggac cacagataat gaaaagagat cagagagcca ggggacagcc ccagccttca    3420
agcagaagct gcaagatgtt catgtggcag agggcaagaa gctgctgctc cagtgccagg    3480
tgtcttctga ccccccagcc accatcatct ggacgctgaa cggaaagacc ctcaagacca    3540
ccaagttcat catcctctcc caggaaggct cactctgctc cgtctccatc gagaaggcac    3600
tgcctgagga cagaggctta tacaagtgtg tagccaagaa tgacgctggc caggcggagt    3660
gctcctgcca agtcaccgtg gatgatgctc cagccagtga gaacaccaag gccccagaga    3720
tgaaatcccg gaggcccaag agctctcttc ctcccgtgct aggaactgag agtgatgcga    3780
ctgtgaaaaa gaaacctgcc cccaagacac ctccgaaggc agcaatgccc ctcagatca    3840 tccagttccc tgaggaccag aaggtacgcg caggagagtc agtggagctg tttggcaaag    3900
tgacaggcac tcagcccatc acctgtacct ggatgaagtt ccgaaagcag atccaggaaa    3960
gcgagcacat gaaggtggag aacagcgaga atggcagcaa gctcaccatc ctggccgcgc    4020
gccaggagca ctgcggctgc tacacactgc tggtggagaa caagctgggc agcaggcagg    4080
cccaggtcaa cctcactgtc gtggataagc cagacccccc agctggcaca ccttgtgcct    4140
ctgacattcg gagctcctca ctgacccgtg cctggtatgg ctcctcatat gatggggca    4200 gtgctgtaca gtcctacagc atcgagatct gggactcagc caacaagacg tggaaggaac    4260
tagccacatg ccgcagcacc tctttcaacg tccaggacct gctgcctgac cacgaatata    4320
agttccgtgt acgtgcaatc aacgtgtatg gaaccagtga gccaagccag gagtctgaac    4380
tcacaacggt aggagagaaa cctgaagagc cgaaggatga agtggaggtg tcagatgatg    4440
atgagaagga gcccgaggtt gattaccgga cagtgacaat caatactgaa caaaaagtat    4500
ctgacttcta cgacattgag gagagattag gatctgggaa atttggacag gtctttcgac    4560
ttgtagaaaa gaaaactcga aaagtctggg cagggaagtt cttcaaggca tattcagcaa    4620
aagagaaaga gaatatccgg caggagatta gcatcatgaa ctgcctccac caccctaagc    4680
tggtccagtg tgtggatgcc tttgaagaaa aggccaacat cgtcatggtc ctggagatcg    4740
tgtcaggagg ggagctgttt gagcgcatca ttgacgagga ctttgagctg acggagcgtg    4800
agtgcatcaa gtacatgcgg cagatctcgg agggagtgga gtacatccac aagcagggca    4860
tcgtgcacct ggacctcaag ccggagaaca tcatgtgtgt caacaagacg ggcaccagga    4920
tcaagctcat cgactttggt ctggccagga ggctggagaa tgcggggtct ctgaaggtcc    4980
tctttggcac cccagaattt gtggctcctg aagtgatcaa ctatgagccc atcggctacg    5040
ccacagacat gtggagcatc gggtcatctc gctacatcct agtcagtggc ctttccccct    5100
tcatgggaga caacgataac gaaaccttgg ccaacgttac ctcagccacc tgggacttcg    5160
acgacgaggc attcgatgag atctccgacg atgccaagga tttcatcagc aatctgctga    5220
agaaagatat gaaaaccgc ctggactgca cgcagtgcct tcagcatcca tggctaatga    5280
aagataccaa gaacatggag gccaagaaac tctccaagga ccggatgaag aagtacatgg    5340
caagaaggaa atggcagaaa cgggcaatg ctgtgagagc cattggaaga ctgtcctcta    5400
tggcaatgat ctcagggctc agtggcagga atcctcaac agggtcacca accagcccgc    5460
tcaatgcaga aaaactagaa tctgaagaag atgtgtccca agctttcctt gaggctgttg    5520
```

```
ctgaggaaaa gcctcatgta aaaccctatt tctctaagac cattcgcgat ttagaagttg    5580
tggagggaag tgctgctaga tttgactgca agattgaagg atacccagac cccgaggttg    5640
tctggttcaa agatgaccag tcaatcaggg agtcccgcca cttccagata gactacgatg    5700
aggacgggaa ctgctctttta attattagtg atgtttgcgg ggatgacgat gccaagtaca    5760
cctgcaaggc tgtcaacagt cttggagaag ccacctgcac agcagagctc attgtggaaa    5820
cgatggagga aggtgaaggg gaaggggaag aggaagaaga gtgaaacaaa gccagagaaa    5880
agcagtttct aagtcatatt aaaaggacta tttctctaaa actca                   5925

<210> SEQ ID NO 3
<211> LENGTH: 5718
<212> TYPE: DNA
<213> ORGANISM: Homo sapiens

<400> SEQUENCE: 3
ccggctgcct ctgctgcagt tcagagcaac ttcaggagct tcccagccga gagcttcagg      60
acgcctttcc tgtcccactg gcccagttgc cacaacaaac aacagagaag acggtgacca     120
tgggggatgt gaagctggtt gcctcgtcac acatttccaa aacctccctc agtgtggatc     180
cctcaagagt tgactccatg cccctgacag aggcccctgc tttcattttg ccccctcgga     240
acctctgcat caaagaagga gccaccgcca agttcgaagg gcgggtccgg ggttacccag     300
agccccaggt gacatggcac agaaacgggc aacccatcac cagcgggggc cgcttcctgc     360
tggattgcgg catccggggg actttcagcc ttgtgattca tgctgtccat gaggaggaca     420
ggggaaagta tacctgtgaa gccaccaatg gcagtggtgc tcgccaggtg acagtggagt     480
tgacagtaga aggaagttttt gcgaagcagc ttggtcagcc tgttgtttcc aaaaccttag     540
gggatagatt ttcagcttca gcagtggaga cccgtcctag catctggggg gagtgcccac     600
caaagtttgc taccaagctg gccgagttg tggtcaaaga aggacagatg ggacgattct     660
cctgcaagat cactggccgg ccccaaccgc aggtcacctg gctcaaggga aatgttccac     720
tgcagccgag tgcccgtgtg tctgtgtctg agaagaacgg catgcaggtt ctggaaatcc     780
atggagtcaa ccaagatgac gtgggagtgt acacgtgcct ggtggtgaac gggtcgggga     840
aggcctcgat gtcagctgaa ctttccatcc aaggtttgga cagtgccaat aggtcatttg     900
tgagagaaac aaaagccacc aattcagatg tcaggaaaga ggtgaccaat gtaatctcaa     960
aggagtcgaa gctggacagt ctggaggctg cagccaaaag caagaactgc tccagccccc    1020
agagaggtgg ctccccaccc tgggctgcaa acagccagcc tcagccccca agggagtcca    1080
agctggagtc atgcaaggac tcgcccagaa cggccccgca gaccccggtc cttcagaaga    1140
cttccagctc catcacccctg caggccgcaa gagttcagcc ggaaccaaga gcaccaggcc    1200
tgggggtcct atcaccttct ggagaagaga ggaagaggcc agctcctccc cgtccagcca    1260
ccttccccac caggcagcct ggcctgggga gccaagatgt tgtgagcaag gctgctaaca    1320
ggagaatccc catggagggc cagagggatt cagcattccc caaatttgag agcaagcccc    1380
aaagccagga ggtcaaggaa atcaaactg tcaagttcag atgtgaaggg cttgccgtga    1440
tggaggtggc cccctccttc tccagtgtcc tgaaggactg cgctgttatt gagggccagg    1500
attttgtgct gcagtgctcc gtacggggga cccccagtgcc ccggatcact tggctgctga    1560
atgggcagcc catccagtac gctcgctcca cctgcgaggc cggcgtggct gagctccaca    1620
tccaggatgc cctgccggag gaccatggca cctacacctg cctagctgag aatgccttgg    1680
ggcaggtgtc ctgcagcgcc tgggtcaccg tccatgaaaa gaagagtagc aggaagagtg    1740
```

```
agtaccttct gcctgtggct cccagcaagc ccactgcacc catcttcctg cagggcctct    1800
ctgatctcaa agtcatggat ggaagccagg tcactatgac tgtccaagtg tcagggaatc    1860
cacccctga agtcatctgg ctgcacaatg ggaatgagat ccaagagtca gaggacttcc     1920
actttgaaca gagaggaact cagcacagcc tttggatcca ggaagtgttc ccggaggaca    1980
cgggcacgta cacctgcgag gcctggaaca gcgctggaga ggtccgcacc caggccgtgc    2040
tcacggtaca agagcctcac gatggcaccc agccctggtt catcagtaag cctcgctcag    2100
tgacagcctc cctgggccag agtgtcctca tctcctgcgc catagctggt gaccccttc    2160
ctaccgtgca ctggctcaga gatggcaaag ccctctgcaa agacactggc cacttcgagg    2220
tgcttcagaa tgaggacgtg ttcaccctgg ttctaaagaa ggtgcagccc tggcatgccg    2280
gccagtatga gatcctgctc aagaaccggg ttggcgaatg cagttgccag gtgtcactga    2340
tgctacagaa cagctctgcc agagcccttc acggggggag ggagcctgcc agctgcgagg    2400
acctctgtgg tggaggagtt ggtgctgatg gtggtggtag tgaccgctat gggtccctga    2460
ggcctggctg gccagcaaga gggcagggtt ggctagagga ggaagacggc gaggacgtgc    2520
gagggtgct aagaggcgc gtggagacga ggcagcacac tgaggaggcg atccgccagc     2580
aggaggtgga gcagctggac ttccgagacc tcctggggaa gaaggtgagt acaaagaccc    2640
tatcggaaga cgacctgaag gagatcccag ccgagcagat ggatttccgt gccaacctgc    2700
agcggcaagt gaagccaaag actgtgtctg aggaagagag gaaggtgcac agcccccagc    2760
aggtcgattt tcgctctgtc ctggccaaga aggggacttc caagaccccc gtgcctgaga    2820
aggtgccacc gccaaaacct gccaccccgg attttcgctc agtgctgggt ggcaagaaga    2880
aattaccagc agagaatggc agcagcagtg ccgagaccct gaatgccaag gcagtggaga    2940
gttccaagcc cctgagcaat gcacagcctt cagggcctt gaaacccgtg ggcaacgcca     3000
agcctgctga gacctgaag ccaatgggca acgccaagcc tgccgagacc ctgaagccca     3060
tgggcaatgc caagcctgat gagaacctga atccgctag caaagaagaa ctcaagaaag     3120
acgttaagaa tgatgtgaac tgcaagagag gccatgcagg gaccacagat aatgaaaaga    3180
gatcagagag ccaggggaca gccccagcct tcaagcagaa gctgcaagat gttcatgtgg    3240
cagagggcaa gaagctgctg ctccagtgcc aggtgtcttc tgacccccca gccaccatca    3300
tctggacgct gaatgaaag accctcaaga ccaccaagtt catcatcctc tcccaggaag     3360
gctcactctg ctccgtctcc atcgagaagg cactgcctga ggacagaggc ttatacaagt    3420
gtgtagccaa gaatgacgct ggccaggcgg agtgctccctg ccaagtcacc gtggatgatg   3480
ctccagccag tgagaacacc aaggcccag agatgaaatc ccggaggccc aagagctctc    3540
ttcctcccgt gctaggaact gagagtgatg cgactgtgaa aaagaaacct gcccccaaga    3600
cacctccgaa ggcagcaatg ccccctcaga tcatccagtt ccctgaggac cagaaggtac    3660
gcgcaggaga gtcagtggag ctgtttggca aagtgacagg cactcagccc atcacctgta    3720
cctggatgaa gttccgaaag cagatccagg aaagcgagca catgaaggtg gagaacagcg    3780
agaatggcag caagctcacc atcctggccg cgcgccagga gcactgcggc tgctacacac    3840
tgctggtgga gaacaagctg ggcagcaggc aggcccaggt caacctcact gtcgtggata    3900
agccagaccc cccagctggc acaccttgtg cctctgacat tcggagctcc tcactgaccc    3960
tgtcctggta tggctcctca tatgatgggg gcagtgctgt acagtcctac agcatcgaga    4020
tctgggactc agccaacaag acgtggaagg aactagccac atgccgcagc acctcttca    4080
acgtccagga cctgctgcct gaccacgaat ataagttccg tgtacgtgca atcaacgtgt    4140
```

```
atggaaccag tgagccaagc caggagtctg aactcacaac ggtaggagag aaacctgaag      4200
agccgaagga tgaagtggag gtgtcagacg atgatgagaa ggagcccgag gttgattacc      4260
ggacagtgac aatcaatact gaacaaaaag tatctgactt ctacgacatt gaggagagat      4320
taggatctgg gaaatttgga caggtctttc gacttgtaga aaagaaaact cgaaaagtct      4380
gggcagggaa gttcttcaag gcatattcag caaagagaa agagaatatc cggcaggaga      4440
ttagcatcat gaactgcctc caccaccta agctggtcca gtgtgtggat gcctttgaag       4500
aaaaggccaa catcgtcatg gtcctggaga tcgtgtcagg aggggagctg tttgagcgca      4560
tcattgacga ggactttgag ctgacggagc gtgagtgcat caagtacatg cggcagatct      4620
cggagggagt ggagtacatc cacaagcagg gcatcgtgca cctggacctc aagccggaga     4680
acatcatgtg tgtcaacaag acgggcacca ggatcaagct catcgacttt ggtctggcca     4740
ggaggctgga gaacgcgggg tctctgaagg tcctcttgg cacccagaa tttgtggctc       4800 ctgaagtgat caactatgag cccatcggct acgccacaga catgtggagc atcgggtca      4860 tctgctacat cctagtcagt ggcctttccc ccttcatggg agacaacgat aacgaaaccct    4920 tggccaacgt tacctcagcc acctgggact tcgacgacga ggcattcgat gagatctccg     4980
acgatgccaa ggatttcatc agcaatctgc tgaagaaga tatgaaaaac cgcctggact     5040
gcacgcagtg ccttcagcat ccatggctaa tgaaagatac caagaacatg gaggccaaga     5100
aactctccaa ggaccggatg aagaagtaca tggcaagaag gaaatggcag aaaacgggca     5160
atgctgtgag agccattgga agactgtcct ctatggcaat gatctcaggg ctcagtggca     5220
ggaaatcctc aacagggtca ccaaccagcc cgctcaatgc agaaaaacta gaatctgaag     5280
aagatgtgtc ccaagctttc cttgaggctg ttgctgagga aaagcctcat gtaaaaccct     5340
atttctctaa gaccattcgc gatttagaag ttgtggaggg aagtgctgct agatttgact     5400
gcaagattga aggataccca gaccccgagg ttgtctggtt caagatgac cagtcaatca     5460 gggagtcccg ccacttccag atagactacg atgaggacgg gaactgctct ttaattatta    5520
gtgatgtttg cggggatgac gatgccaagt acacctgcaa ggctgtcaac agtcttggag    5580
aagccacctg cacagcagag ctcattgtgg aaacgatgga ggaaggtgaa ggggaagggg    5640
aagaggaaga agagtgaaac aaagccagag aaaagcagtt tctaagtcat attaaaagga    5700
ctatttctct aaaactca                                                   5718

<210> SEQ ID NO 4
<211> LENGTH: 5772
<212> TYPE: DNA
<213> ORGANISM: Homo sapiens

<400> SEQUENCE: 4
ccggctgcct ctgctgcagt tcagagcaac ttcaggagct tcccagccga gagcttcagg       60
acgcctttcc tgtcccactg gcccagttgc cacaacaaac aacagagaag acggtgacca      120 tggggatgt gaagctggtt gcctcgtcac acatttccaa aacctccctc agtgtggatc       180
cctcaagagt tgactccatg cccctgacag aggcccctgc tttcattttg cccccctcgga    240 acctctgcat caaagaagga gccaccgcca gttcgaagg gcgggtccgg ggttacccag      300
agccccaggt gacatggcac agaaacgggc aacccatcac cagcggggc cgcttcctgc     360 tggattgcgg catccggggg actttcagcc ttgtgattca tgctgtccat gaggaggaca     420
ggggaaagta tacctgtgaa gccaccaatg cagtggtgc tcgccaggtg acagtggagt      480
tgacagtaga aggaagtttt gcgaagcagc ttggtcagcc tgttgtttcc aaaaccttag     540
```

| | | |
|---|---|---|
| gggatagatt tcagcttca gcagtggaga cccgtcctag catctggggg gagtgcccac | 600 |
| caaagtttgc taccaagctg ggccgagttg tggtcaaaga aggacagatg ggacgattct | 660 |
| cctgcaagat cactggccgg ccccaaccgc aggtcacctg gctcaaggga aatgttccac | 720 |
| tgcagccgag tgcccgtgtg tctgtgtctg agaagaacgg catgcaggtt ctggaaatcc | 780 |
| atggagtcaa ccaagatgac gtgggagtgt acacgtgcct ggtggtgaac gggtcgggga | 840 |
| aggcctcgat gtcagctgaa cttccatcc aaggtttgga cagtgccaat aggtcatttg | 900 |
| tgagagaaac aaaagccacc aattcagatg tcaggaaaga ggtgaccaat gtaatctcaa | 960 |
| aggagtcgaa gctggacagt ctggaggctg cagccaaaag caagaactgc tccagccccc | 1020 |
| agagaggtgg ctccccaccc tgggctgcaa acagccagcc tcagccccca agggagtcca | 1080 |
| agctggagtc atgcaaggac tcgcccagaa cggccccgca gaccccggtc cttcagaaga | 1140 |
| cttccagctc catcaccctg caggccgcaa gagttcagcc ggaaccaaga gcaccaggcc | 1200 |
| tgggggtcct atcaccttct ggagaagaga ggaagaggcc agctcctccc cgtccagcca | 1260 |
| ccttccccac caggcagcct ggcctgggga gccaagatgt tgtgagcaag gctgctaaca | 1320 |
| ggagaatccc catggagggc cagagggatt cagcattccc caaatttgag agcaagcccc | 1380 |
| aaagccagga ggtcaaggaa aatcaaactg tcaagttcag atgtgaagtt tccgggattc | 1440 |
| caaagcctga agtggcctgg ttcctggaag cacccccgt gaggagacag gaaggcagca | 1500 |
| ttgaggttta tgaagatgct ggctcccatt acctctgcct gctgaaagcc cggaccaggg | 1560 |
| acagtgggac atacagctgc actgcttcca acgcccaagg ccaggtgtcc tgtagctgga | 1620 |
| ccctccaagt ggaaaggctt gccgtgatgg aggtggcccc ctccttctcc agtgtcctga | 1680 |
| aggactgcgc tgttattgag ggccaggatt ttgtgctgca gtgctccgta cgggggaccc | 1740 |
| cagtgccccg gatcacttgg ctgctgaatg ggcagcccat ccagtacgct cgctccacct | 1800 |
| gcgaggccgg cgtggctgag ctccacatcc aggatgccct gccggaggac catggcacct | 1860 |
| acacctgcct agctgagaat gccttggggc aggtgtcctg cagcgcctgg gtcaccgtcc | 1920 |
| atgaaaagaa gagtagcagg aagagtgagt accttctgcc tgtggctccc agcaagccca | 1980 |
| ctgcacccat cttcctgcag ggcctctctg atctcaaagt catggatgga agccaggtca | 2040 |
| ctatgactgt ccaagtgtca gggaatccac cccctgaagt catctggctg cacaatggaa | 2100 |
| atgagatcca agagtcagag gacttccact ttgaacagag aggaactcag cacagccttt | 2160 |
| ggatccagga agtgttcccg gaggacacgg gcacgtacac ctgcgaggcc tggaacagcg | 2220 |
| ctggagaggt ccgcacccag gccgtgctca cggtacaaga gcctcacgat ggcacccagc | 2280 |
| cctggttcat cagtaagcct cgctcagtga cagcctccct gggccagagt gtcctcatct | 2340 |
| cctgcgccat agctggtgac ccctttccta ccgtgcactg gctcagagat ggcaaagccc | 2400 |
| tctgcaaaga cactggccac ttcgaggtgc ttcagaatga ggacgtgttc acctggttc | 2460 |
| taaagaaggt gcagccctgg catgccggcc agtatgagat cctgctcaag aaccggttg | 2520 |
| gcgaatgcag ttgccaggtg tcactgatgc tacagaacag ctctgccaga gcccttccac | 2580 |
| ggggagggga gcctgccagc tgcgaggacc tctgtggtgg aggagttggt gctgatggtg | 2640 |
| gtggtagtga ccgctatggg tccctgaggc ctggctggcc agcaagaggg cagggttggc | 2700 |
| tagaggagga agacggcgag gacgtgcgag gggtgctgaa gaggcgcgtg gagacgaggc | 2760 |
| agcacactga ggaggcgatc cgccagcagg aggtggagca gctggacttc cgagacctcc | 2820 |
| tggggaagaa ggtgagtaca aagacccat cggaagacga cctgaaggag atcccggccg | 2880 |
| agcagatgga tttccgtgcc aacctgcagc ggcaagtgaa gccaaagact gtgtctgagg | 2940 |

```
aagagaggaa ggtgcacagc ccccagcagg tcgattttcg ctctgtcctg gccaagaagg      3000
ggacttccaa gaccccgtg cctgagaagg tgccaccgcc aaaacctgcc accccggatt       3060
ttcgctcagt gctgggtggc aagaagaaat taccagcaga gaatggcagc agcagtgccg      3120
agaccctgaa tgccaaggca gtggagagtt ccaagcccct gagcaatgca cagccttcag      3180
ggcccttgaa acccgtgggc aacgccaagc ctgctgagac cctgaagcca tgggcaacg      3240 ccaagcctgc cgagaccctg aagcccatgg gcaatgccaa gcctgatgag aacctgaaat     3300
ccgctagcaa agaagaactc aagaaagacg ttaagaatga tgtgaactgc aagagaggcc      3360
atgcagggac cacagataat gaaaagagat cagagagcca ggggacagcc ccagccttca      3420
agcagaagct gcaagatgtt catgtggcag agggcaagaa gctgctgctc cagtgccagg      3480
tgtcttctga cccccagcc accatcatct ggacgctgaa tggaaagacc ctcaagacca       3540
ccaagttcat catcctctcc caggaaggct cactctgctc cgtctccatc gagaaggcac      3600
tgcctgagga cagaggctta tacaagtgtg tagccaagaa tgacgctggc caggcggagt     3660
gctcctgcca agtcaccgtg gatgatgctc cagccagtga gaacaccaag gccccagaga     3720
tgaaatcccg gaggcccaag agctctcttc ctcccgtgct aggaactgag agtgatgcga     3780
ctgtgaaaaa gaaacctgcc cccaagacac ctccgaaggc agcaatgccc cctcagatca     3840
tccagttccc tgaggaccag aaggtacgcg caggagagtc agtggagctg tttggcaaag     3900
tgacaggcac tcagcccatc acctgtacct ggatgaagtt ccgaaagcag atccaggaaa     3960
gcgagcacat gaaggtggag aacagcgaga atgcagcaa gctcaccatc ctggccgcgc      4020
gccaggagca ctgcggctgc tacacactgc tggtggagaa caagctgggc agcaggcagg    4080
cccaggtcaa cctcactgtc gtggataagc cagaccccc agctggcaca ccttgtgcct     4140
ctgacattcg gagctcctca ctgaccctgt cctggtatgg ctcctcatat gatggggca    4200 gtgctgtaca gtcctacagc atcgagatct gggactcagc caacaagacg tggaaggaac    4260
tagccacatg ccgcagcacc tctttcaacg tccaggacct gctgcctgac cacgaatata    4320
agttccgtgt acgtgcaatc aacgtgtatg gaaccagtga gccaagccag gagtctgaac    4380
tcacaacggt aggagagaaa cctgaagagc cgaaggatga agtggaggtg tcagatgatg    4440
atgagaagga gcccgaggtt gattaccgga cagtgacaat caatactgaa caaaaagtat    4500
ctgacttcta cgacattgag gagagattag gatctgggaa attggacag gtcttcgac      4560 ttgtagaaaa gaaaactcga aaagtctggg cagggaagtt cttcaaggca tattcagcaa    4620
aagagaaaga gaatatccgg caggagatta gcatcatgaa ctgcctccac caccctaagc    4680
tggtccagtg tgtggatgcc tttgaagaaa aggccaacat cgtcatggtc ctggagatcg    4740
tgtcaggagg ggagctgttt gagcgcatca ttgacgagga ctttgagctg acggagcgtg    4800
agtgcatcaa gtacatgcgg cagatctcgg agggagtgga gtacatccac aagcagggca    4860
tcgtgcacct ggacctcaag ccggagaaca tcatgtgtgt caacaagacg ggcaccagga    4920
tcaagctcat cgactttggt ctggccagga ggctggagaa cgcggggtct ctgaaggtcc    4980
tctttggcac cccagaattt gtggctcctg aagtgatcaa ctatgagccc atcggctacg    5040
ccacagacat gtggagcatc ggggtcatct gctacatcct aaaccgcctg gactgcacgc    5100
agtgccttca gcatccatgg ctaatgaaag ataccaagaa catggaggcc aagaaactct    5160
ccaaggaccg gatgaagaag tacatggcaa gaaggaaatg gcagaaaacg ggcaatgctg    5220
tgagagccat tggaagactg tcctctatgg caatgatctc agggctcagt ggcaggaaat    5280
cctcaacagg gtcaccaacc agcccgctca atgcagaaaa actagaatct gaagaagatg    5340
```

```
tgtcccaagc tttccttgag gctgttgctg aggaaaagcc tcatgtaaaa ccctatttct    5400
ctaagaccat tcgcgattta gaagttgtgg agggaagtgc tgctagattt gactgcaaga    5460
ttgaaggata cccagacccc gaggttgtct ggttcaaaga tgaccagtca atcagggagt    5520
cccgccactt ccagatagac tacgatgagg acgggaactg ctctttaatt attagtgatg    5580
tttgcgggga tgacgatgcc aagtacacct gcaaggctgt caacagtctt ggagaagcca    5640
cctgcacagc agagctcatt gtggaaacga tggaggaagg tgaaggggaa ggggaagagg    5700
aagaagagtg aaacaaagcc agagaaaagc agtttctaag tcatattaaa aggactattt    5760
ctctaaaact ca                                                        5772
```

<210> SEQ ID NO 5
<211> LENGTH: 5565
<212> TYPE: DNA
<213> ORGANISM: Homo sapiens

<400> SEQUENCE: 5

```
ccggctgcct ctgctgcagt tcagagcaac ttcaggagct tcccagccga gagcttcagg      60
acgcctttcc tgtcccactg gcccagttgc acaacaaac aacagagaag acggtgacca     120
tgggggatgt gaagctggtt gcctcgtcac acatttccaa aacctccctc agtgtggatc     180
cctcaagagt tgactccatg cccctgacag aggcccctgc tttcattttg cccccctcgga    240 acctctgcat caaagaagga gccaccgcca agttcgaagg gcgggtccgg ggttacccag     300
agccccaggt gacatggcac agaaacgggc aacccatcac cagcgggggc cgcttcctgc     360
tggattgcgg catccggggg actttcagcc ttgtgattca tgctgtccat gaggaggaca     420
ggggaaagta tacctgtgaa gccaccaatg gcagtggtgc tcgccaggtg acagtggagt     480
tgacagtaga aggaagtttt gcgaagcagc ttggtcagcc tgttgtttcc aaaaccttag     540
gggatagatt ttcagcttca gcagtggaga cccgtcctag catctggggg gagtgcccac     600
caaagtttgc taccaagctg ggccgagttg tggtcaaaga aggacagatg ggacgattct     660
cctgcaagat cactggccgg ccccaaccgc aggtcacctg gctcaaggga atgttccac      720 tgcagccgag tgcccgtgtg tctgtgtctg agaagaacgg catgcaggtt ctggaaatcc     780
atggagtcaa ccaagatgac gtgggagtgt acacgtgcct ggtggtgaac gggtcgggga    840
aggcctcgat gtcagctgaa cttttccatcc aaggtttgga cagtgccaat aggtcatttg    900
tgagagaaac aaaaagccacc aattcagatg tcaggaaaga ggtgaccaat gtaatctcaa    960
aggagtcgaa gctggacagt ctggaggctg cagccaaaag caagaactgc tccagccccc    1020
agagaggtgg ctccccaccc tgggctgcaa acagccagcc tcagccccca agggagtcca    1080
agctggagtc atgcaaggac tcgcccagaa cggccccgca gaccccggtc cttcagaaga    1140
cttccagctc catcacccctg caggccgcaa gagttcagcc ggaaccaaga gcaccaggcc    1200
tgggggtcct atcaccttct ggagaagaga ggaagaggcc agctcctccc cgtccagcca    1260
ccttccccac caggcagcct ggcctgggga gccaagatgt tgtgagcaag gctgctaaca    1320
ggagaatccc catggagggc cagagggatt cagcattccc caaatttgag agcaagcccc    1380
aaagccagga ggtcaaggaa aatcaaactg tcaagttcag atgtgaaggg cttgccgtga    1440
tggaggtggc cccctccttc tccagtgtcc tgaaggactg cgctgttatt gagggccagg    1500
attttgtgct gcagtgctcc gtacggggga ccccagtgcc ccggatcact tggctgctga    1560
atgggcagcc catccagtac gctcgctcca cctgcgaggc cggcgtggct gagctccaca    1620
tccaggatgc cctgccggag gaccatggca cctacacctg cctagctgag aatgccttgg    1680
```

```
ggcaggtgtc ctgcagcgcc tgggtcaccg tccatgaaaa gaagagtagc aggaagagtg   1740
agtaccttct gcctgtggct cccagcaagc ccactgcacc catcttcctg cagggcctct   1800
ctgatctcaa agtcatggat ggaagccagg tcactatgac tgtccaagtg tcagggaatc   1860
cacccctga agtcatctgg ctgcacaatg ggaatgagat ccaagagtca gaggacttcc    1920
actttgaaca gagaggaact cagcacagcc tttggatcca ggaagtgttc ccggaggaca   1980
cgggcacgta cacctgcgag gcctggaaca gcgctggaga ggtccgcacc caggccgtgc   2040
tcacggtaca agagcctcac gatggcaccc agccctggtt catcagtaag cctcgctcag   2100
tgacagcctc cctgggccag agtgtcctca tctcctgcgc catagctggt gacccctttc   2160
ctaccgtgca ctggctcaga gatggcaaag ccctctgcaa agacactggc cacttcgagg   2220
tgcttcagaa tgaggacgtg ttcaccctgg ttctaaagaa ggtgcagccc tggcatgccg   2280
gccagtatga gatcctgctc aagaaccggg ttggcgaatg cagttgccag gtgtcactga   2340
tgctacagaa cagctctgcc agagcccttc acgggggag ggagcctgcc agctgcgagg    2400
acctctgtgg tggaggagtt ggtgctgatg gtggtggtag tgaccgctat gggtccctga   2460
ggcctggctg gccagcaaga gggcagggtt ggctagagga ggaagacggc gaggacgtgc   2520
gagggtgct gaagaggcgc gtggagacga ggcagcacac tgaggaggcg atccgccagc    2580
aggaggtgga gcagctggac ttccgcgacc tcctgggcaa gaaggtgagt acaaagaccc   2640
tatcggaaga cgacctgaag gagatcccgg ccgagcagat ggatttccgt gccaacctgc   2700
agcggcaagt gaagccaaag actgtgtctg aggaagagag gaaggtgcac agcccccagc   2760
aggtcgattt tcgctctgtc ctggccaaga aggggacttc caagaccccc gtgcctgaga   2820
aggtgccacc gccaaaaacct gccaccccgg attttcgctc agtgctgggt ggcaagaaga   2880
aattaccagc agagaatggc agcagcagtg ccgagaccct gaatgccaag gcagtggaga   2940
gttccaagcc cctgagcaat gcacagcctt cagggccctt gaaacccgtg ggcaacgcca   3000
agcctgctga gaccctgaag ccaatgggca acgccaagcc tgccgagacc ctgaagccca   3060
tgggcaatgc caagcctgat gagaacctga atccgctag caaagaagaa ctcaagaaag    3120
acgttaagaa tgatgtgaac tgcaagagag ccatgcagg gaccacagat aatgaaaaga    3180
gatcagagag ccaggggaca gccccagcct tcaagcagaa gctgcaagat gttcatgtgg   3240
cagagggcaa gaagctgctg ctccagtgcc aggtgtcttc tgaccccca gccaccatca    3300
tctggacgct gaatggaaag accctcaaga ccaccaagtt catcatcctc tcccaggaag   3360
gctcactctg ctccgtctcc atcgagaagg cactgcctga ggacagaggc ttatacaagt   3420
gtgtagccaa gaatgacgct ggccaggcgg agtgctcctg ccaagtcacc gtggatgatg   3480
ctccagccag tgagaacacc aaggcccag agatgaaatc ccggaggccc aagagctctc    3540
ttcctcccgt gctaggaact gagagtgatg cgactgtgaa aaagaaacct gcccccaaga   3600
cacctccgaa ggcagcaatg ccccctcaga tcatccagtt ccctgaggac cagaaggtac   3660
gcgcaggaga gtcagtggag ctgtttggca aagtgacagg cactcagccc atcacctgta   3720
cctggatgaa gttccgaaag cagatccagg aaagcgagca catgaaggtg gagaacagcg   3780
agaatggcag caagctcacc atcctggccg cgcgccagga gcactgcggc tgctacacac   3840
tgctggtgga gaacaagctg ggcagcaggc aggcccaggt caacctcact gtcgtggata   3900
agccagaccc cccagctggc acaccttgtg cctctgacat tcggagctcc tcactgaccc   3960
tgtcctggta tggctcctca tatgatgggg gcagtgctgt acagtcctac agcatcgaga   4020
tctgggactc agccaacaag acgtggaagg aactagccac atgccgcagc acctctttca   4080
```

-continued

| | |
|---|---|
| acgtccagga cctgctgcct gaccacgaat ataagttccg tgtacgtgca atcaacgtgt | 4140 |
| atggaaccag tgagccaagc caggagtctg aactcacaac ggtaggagag aaacctgaag | 4200 |
| agccgaagga tgaagtggag gtgtcagatg atgatgagaa ggagcccgag gttgattacc | 4260 |
| ggacagtgac aatcaatact gaacaaaaag tatctgactt ctacgacatt gaggagagat | 4320 |
| taggatctgg gaaatttgga caggtctttc gacttgtaga aaagaaaact cgaaaagtct | 4380 |
| gggcagggaa gttcttcaag gcatattcag caaaagagaa agagaatatc cggcaggaga | 4440 |
| ttagcatcat gaactgcctc caccacccta agctggtcca gtgtgtggat gcctttgaag | 4500 |
| aaaaggccaa catcgtcatg gtcctggaga tcgtgtcagg aggggagctg tttgagcgca | 4560 |
| tcattgacga ggactttgag ctgacggagc gtgagtgcat caagtacatg cggcagatct | 4620 |
| cggagggagt ggagtacatc cacaagcagg gcatcgtgca cctggacctc aagccggaga | 4680 |
| acatcatgtg tgtcaacaag acgggcacca ggatcaagct catcgacttt ggtctggcca | 4740 |
| ggaggctgga gaacgcgggg tctctgaagg tcctctttgg cacccagaa tttgtggctc | 4800 |
| ctgaagtgat caactatgag cccatcgacg ccacagacat gtggagcatc ggggtcatct | 4860 |
| gctacatcct aaaccgcctg gactggctca cgcagtgcct tcagcatcca tggctaatga | 4920 |
| aagataccaa gaacatggag gccaagaaac tctccaagga ccggatgaag aagtacatgg | 4980 |
| caagaaggaa atggcagaaa acgggcaatg ctgtgagagc cattggaaga ctgtcctcta | 5040 |
| tggcaatgat ctcagggctc agtggcagga atcctcaac agggtcacca accagcccgc | 5100 |
| tcaatgcaga aaaactagaa tctgaagaag atgtgtccca agctttcctt gaggctgttg | 5160 |
| ctgaggaaaa gcctcatgta aaaccctatt tctctaagac cattcgcgat ttagaagttg | 5220 |
| tggagggaag tgctgctaga tttgactgca agattgaagg atacccagac cccgaggttg | 5280 |
| tctggttcaa agatgaccag tcaatcaggg agtcccgcca cttccagata gactacgatg | 5340 |
| aggacgggaa ctgctcttta attattagtg atgtttgcgg ggatgacgat gccaagtaca | 5400 |
| cctgcaaggc tgtcaacagt cttggagaag ccacctgcac agcagagctc attgtggaaa | 5460 |
| cgatggagga aggtgaaggg gaaggggaag aggaagaaga gtgaaacaaa gccagagaaa | 5520 |
| agcagtttct aagtcatatt aaaaggacta tttctctaaa actca | 5565 |

<210> SEQ ID NO 6
<211> LENGTH: 5713
<212> TYPE: DNA
<213> ORGANISM: Homo sapiens

<400> SEQUENCE: 6

| | |
|---|---|
| gcagagcccg gctgcctctg ctgcagttca gagcaacttc aggagcttcc cagccgagag | 60 |
| cttcaggacg cctttcctgt cccactggcc cagttgccac aacaaacaac agagaagacg | 120 |
| gtgaccatgg gggatgtgaa gctggttgcc tcgtcacaca tttccaaaac ctccctcagt | 180 |
| gtggatccct caagagttga ctccatgccc ctgacagagg cccctgcttt cattttgccc | 240 |
| cctcggaacc tctgcatcaa agaaggagcc accgccaagt tcgaagggcg ggtccggggt | 300 |
| tacccagagc cccaggtgac atggcacaga aacgggcaac ccatcaccag cggggggccgc | 360 |
| ttcctgctgg attgcggcat ccggggggact ttcagccttg tgattcatgc tgtccatgag | 420 |
| gaggacaggg gaaagtatac ctgtgaagcc accaatggca gtggtgctcg ccaggtgaca | 480 |
| gtggagttga cagtagaagg aagttttgcg aagcagcttg gtcagcctgt tgtttccaaa | 540 |
| accttagggg atagattttc agcttcagca gtggagaccc gtcctagcat ctgggggggag | 600 |
| tgcccaccaa agtttgctac caagctgggc cgagttgtgg tcaaagaagg acagatggga | 660 |

```
cgattctcct gcaagatcac tggccggccc caaccgcagg tcacctggct caagggaaat    720
gttccactgc agccgagtgc ccgtgtgtct gtgtctgaga agaacggcat gcaggttctg    780
gaaatccatg gagtcaacca agatgacgtg ggagtgtaca cgtgcctggt ggtgaacggg    840
tcggggaagg cctcgatgtc agctgaactt tccatccaag gtttggacag tgccaatagg    900
tcatttgtga gagaaacaaa agccaccaat tcagatgtca ggaagaggt gaccaatgta     960
atctcaaagg agtcgaagct ggacagtctg gaggctgcag ccaaaagcaa gaactgctcc   1020
agcccccaga gaggtggctc cccaccctgg gctgcaaaca gccagcctca gcccccaagg   1080
gagtccaagc tggagtcatg caaggactcg cccagaacgg ccccgcagac cccggtcctt   1140
cagaagactt ccagctccat caccctgcag gccgcaagag ttcagccgga accaagagca   1200
ccaggcctgg gggtcctatc accttctgga agagagga agaggccagc tcctccccgt     1260
ccagccacct tccccaccag gcagcctggc ctggggagcc aagatgttgt gagcaaggct   1320
gctaacagga gaatccccat ggagggccag agggattcag cattccccaa atttgagagc   1380
aagcccaaa gccaggaggt caaggaaat caaactgtca agttcagatg tgaagtttcc     1440
gggattccaa agcctgaagt ggcctggttc ctggaaggca ccccgtgag gagacaggaa    1500
ggcagcattg aggtttatga agatgctggc tcccattacc tctgcctgct gaaagcccgg   1560
accagggaca gtgggacata cagctgcact gcttccaacg cccaaggcca ggtgtcctgt   1620
agctggaccc tccaagtgga aaggcttgcc gtgatggagg tggccccctc cttctccagt   1680
gtcctgaagg actgcgctgt tattgagggc caggattttg tgctgcagtg ctccgtacgg   1740
gggaccccag tgccccggat cacttggctg ctgaatgggc agcccatcca gtacgctcgc   1800
tccacctgcg aggccggcgt ggctgagctc acatccagg atgccctgcc ggaggaccat    1860
ggcacctaca cctgcctagc tgagaatgcc ttggggcagg tgtcctgcag cgcctgggtc   1920
accgtccatg aaaagaagag tagcaggaag agtgagtacc ttctgcctgt ggctcccagc   1980
aagcccactg cacccatctt cctgcagggc ctctctgatc tcaaagtcat ggatggaagc   2040
caggtcacta tgactgtcca agtgtcaggg aatccacccc ctgaagtcat ctggctgcac   2100
aatgggaatg agatccaaga gtcagaggac ttccactttg aacagagagg aactcagcac   2160
agcctttgga tccaggaagt gttcccggag gacacgggca cgtacacctg cgaggcctgg   2220
aacagcgctg gagaggtccg cacccaggcc gtgctcacgg tacaagagcc tcacgatggc   2280
acccagccct ggttcatcag taagcctcgc tcagtgacag cctccctggg ccagagtgtc   2340
ctcatctcct gcgccatagc tggtgacccc tttcctaccg tgcactggct cagagatggc   2400
aaagccctct gcaaagacac tggccacttc gaggtgcttc agaatgagga cgtgttcacc   2460
ctggttctaa agaaggtgca gcctggcat gccggccagt atgagatcct gctcaagaac   2520
cgggttggcg aatgcagttg ccaggtgtca ctgatgctac agaacagctc tgccagagcc   2580
cttccacggg ggaggagcc tgccagctgc gaggacctct gtggtggagg agttggtgct   2640
gatggtggtg gtagtgaccg ctatgggtcc ctgaggcctg gctggccagc aagagggcag   2700
ggttggctag aggaggaaga cggcgaggac gtgcgagggg tgctgaagag gcgcgtggag   2760
acgaggcagc acactgagga ggcgatccgc cagcaggagg tggagcagct ggacttccga   2820
gacctcctgg ggaagaaggt gagtacaaag accctatcgg aagacgacct gaaggagatc   2880
ccggccgagc agatggattt ccgtgccaac ctgcagcggc aagtgaagcc aaagactgtg   2940
tctgaggaag agaggaaggt gcacagcccc cagcaggtcg attttcgctc tgtcctggcc   3000
aagaagggga cttccaagac ccccgtgcct gagaaggtgc caccgccaaa acctgccacc   3060
```

-continued

```
ccggattttc gctcagtgct gggtggcaag aagaaattac cagcagagaa tggcagcagc    3120
agtgccgaga ccctgaatgc caaggcagtg gagagttcca agcccctgag caatgcacag    3180
ccttcagggc ccttgaaacc cgtgggcaac gccaagcctg ctgagaccct gaagccaatg    3240
ggcaacgcca agcctgccga gaccctgaag cccatgggca atgccaagcc tgatgagaac    3300
ctgaaatccg ctagcaaaga agaactcaag aaagacgtta agaatgatgt gaactgcaag    3360
agaggccatg cagggaccac agataatgaa agagatcag agagccaggg gacagcccca    3420
gccttcaagc agaagctgca agatgttcat gtggcagagg gcaagaagct gctgctccag    3480
tgccaggtgt cttctgaccc cccagccacc atcatctgga cgctgaatgg aaagaccctc    3540
aagaccacca agttcatcat cctctcccag gaaggctcac tctgctccgt ctccatcgag    3600
aaggcactgc ctgaggacag aggcttatac aagtgtgtag ccaagaatga cgctggccag    3660
gcggagtgct cctgccaagt caccgtggat gatgctccag ccagtgagaa caccaaggcc    3720
ccagagatga atcccggag gcccaagagc tctcttcctc ccgtgctagg aactgagagt    3780
gatgcgactg tgaaaaagaa acctgccccc aagacacctc cgaaggcagc aatgccccct    3840
cagatcatcc agttccctga ggaccagaag gtacgcgcag gagagtcagt ggagctgttt    3900
ggcaaagtga caggcactca gcccatcacc tgtacctgga tgaagttccg aaagcagatc    3960
caggaaagcg agcacatgaa ggtggagaac agcgagaatg gcagcaagct caccatcctg    4020
gccgcgcgcc aggagcactg cggctgctac acactgctgg tggagaacaa gctgggcagc    4080
aggcaggccc aggtcaacct cactgtcgtg ataagccag accccccagc tggcacacct    4140
tgtgcctctg acattcggag ctcctcactg accctgtcct ggtatggctc ctcatatgat    4200
gggggcagtg ctgtacagtc ctacagcatc gagatctggg actcagccaa caagacgtgg    4260
aaggaactag ccacatgccg cagcacctct ttcaacgtcc aggacctgct gcctgaccac    4320
gaatataagt tccgtgtacg tgcaatcaac cgtgtatgga accagtgagcc aagccaggag    4380 tctgaactca caacggtagg agagaaacct gaagagccga aggatgaagt ggaggtgtca    4440
gatgatgatg agaaggagcc cgaggttgat taccggacag tgacaatcaa tactgaacaa    4500
aaagtatctg acttctacga cattgaggag agattaggat cgctgtttga gcgcatcatt    4560
gacgaggact ttgagctgac ggagcgtgag tgcatcaagt acatgcggca gatctcggag    4620
ggagtggagt acatccacaa gcagggcatc gtgcacctgg acctcaagcc ggagaacatc    4680
atgtgtgtca acaagacggg caccaggatc aagctcatcg actttggtct ggccaggagg    4740
ctggagaacg cggggtctct gaaggtcctc tttggcaccc cagaatttgt ggctcctgaa    4800
gtgatcaact atgagcccat cggctacgcc acagacatgt ggagcatcgg ggtcatctgc    4860
tacatcctag tcagtggcct ttcccccttc atgggagaca cgataacga aaccttggcc    4920 aacgttacct cagccacctg ggacttcgac gacgaggcat tcgatgagat ctccgacgat    4980
gccaaggatt tcatcagcaa tctgctgaag aaagatatga aaaccgcct ggactgcacg    5040 cagtgccttc agcatccatg gctaatgaaa gataccaaga acatggaggc caagaaactc    5100
tccaaggacc ggatgaagaa gtacatggca agaaggaaat ggcagaaaac gggcaatgct    5160
gtgagagcca ttggaagact gtcctctatg gcaatgatct cagggctcag tggcaggaaa    5220
tcctcaacag ggtcaccaac cagcccgctc aatcagaaaa actagaatc tgaagaagat    5280 gtgtcccaag cttccttga ggctgttgct gaggaaaagc ctcatgtaaa accctatttc    5340
tctaagacca ttcgcgattt agaagttgtg gagggaagtg ctgctagatt tgactgcaag    5400
attgaaggat acccagaccc cgaggttgtc tggttcaaag atgaccagtc aatcagggag    5460
```

-continued

| | | |
|---|---|---|
| tcccgccact tccagataga ctacgatgag gacgggaact gctctttaat tattagtgat | 5520 |
| gtttgcgggg atgacgatgc caagtacacc tgcaaggctg tcaacagtct ggagaagcc | 5580 |
| acctgcacag cagagctcat tgtggaaacg atggaggaag gtgaagggga aggggaagag | 5640 |
| gaagaagagt gaaacaaagc cagagaaaag cagtttctaa gtcatattaa aaggactatt | 5700 |
| tctctaaaac tca | 5713 |

<210> SEQ ID NO 7
<211> LENGTH: 3181
<212> TYPE: DNA
<213> ORGANISM: Homo sapiens

<400> SEQUENCE: 7

| | | |
|---|---|---|
| agcacactga ggaggcgatc cgcagcagga ggtggagcag ctggacttcc gagacctcct | 60 |
| ggggaagaag gtgagtacaa agaccctatc ggaagacgac ctgaaggaga tcccagccga | 120 |
| gcagatggat ttccgtgcca acctgcacgc gcaagtgaag ccaaagactg tgtctgagga | 180 |
| agagaggaag gtgcacagcc cccagcaggt cgattttcgc tctgtcctgg ccaagaaggg | 240 |
| gacttccaag acccccgtgc ctgagaaggt gccaccgcca aaacctgcca ccccggattt | 300 |
| tcgctcagtg ctgggtggca agaagaaatt accagcagag aatggcagca gcagtgccga | 360 |
| gaccctgaat gccaaggcag tggagagttc caagcccctg agcaatgcac agccttcagg | 420 |
| gcccttgaaa cccgtgggca cgccaagcc tgctgagacc ctgaagccaa tgggcaacgc | 480 |
| caagcctgcc gagaccctga agcccatggg caatgccaag cctgatgaga acctgaaatc | 540 |
| cgctagcaaa gaagaactca gaaagacgt taagaatgat gtgaactgca agagaggcca | 600 |
| tgcagggacc acagataatg aaaagagatc agagagccag gggacagccc cagccttcaa | 660 |
| gcagaagctg caagatgttc atgtggcaga gggcaagaag ctgctgctcc agtgccaggt | 720 |
| gtcttctgac ccccccagcca ccatcatctg gacgctgaac ggaaagaccc tcaagaccac | 780 |
| caagttcatc atcctctccc aggaaggctc actctgctcc gtctccatcg agaaggcact | 840 |
| gcctgaggac agaggcttat acaagtgtgt agccaagaat gacgctggcc aggcggagtg | 900 |
| ctcctgccaa gtcaccgtgg atgatgctcc agccagtgag aacaccaagg ccccagagat | 960 |
| gaaatcccgg aggcccaaga gctctcttcc tcccgtgcta ggaactgaga gtgatgcgac | 1020 |
| tgtgaaaaag aaacctgccc ccaagacacc tccgaaggca gcaatgcccc ctcagatcat | 1080 |
| ccagttccct gaggaccaga aggtacgcgc aggagagtca gtggagctgt ttggcaaagt | 1140 |
| gacaggcact cagcccatca cctgtacctg gatgaagttc cgaaagcaga tccaggaaag | 1200 |
| cgagcacatg aaggtggaga acagcgagaa tggcagcaag ctcaccatcc tggccgcgcg | 1260 |
| ccaggagcac tgcggctgct acacactgct ggtggagaac aagctgggca gcaggcaggc | 1320 |
| ccaggtcaac ctcactgtcg tggataagcc agaccccca gctggcacac cttgtgcctc | 1380 |
| tgacattcgg agctcctcac tgaccctgtc ctggtatggc tcctcatatg atggggcag | 1440 |
| tgctgtacag tcctacagca tcgagatctg ggactcagcc aacaagacgt ggaaggaact | 1500 |
| agccacatgc cgcagcacct ctttcaacgt ccaggacctg ctgcctgacc acgaatataa | 1560 |
| gttccgtgta cgtgcaatca acgtgtatgg aaccagtgag ccaagccagg agtctgaact | 1620 |
| cacaacggta ggagagaaac ctgaagagcc gaaggatgaa gtgaggtgt cagatgatga | 1680 |
| tgagaaggag cccgaggttg attaccggac agtgacaatc aatactgaac aaaaagtatc | 1740 |
| tgacttctac gacattgagg agagattagg atctgggaaa tttggacagg tctttcgact | 1800 |
| tgtagaaaag aaaactcgaa aagtctgggc agggaagttc ttcaaggcat attcagcaaa | 1860 |

```
agagaaagag aatatccggc aggagattag catcatgaac tgcctccacc accctaagct   1920
ggtccagtgt gtggatgcct ttgaagaaaa ggccaacatc gtcatggtcc tggagatcgt   1980
gtcaggaggg gagctgtttg agcgcatcat tgacgaggac tttgagctga cggagcgtga   2040
gtgcatcaag tacatgcggc agatctcgga gggagtggag tacatccaca agcagggcat   2100
cgtgcacctg gacctcaagc cggagaacat catgtgtgtc aacaagacgg gcaccaggat   2160
caagctcatc gactttggtc tggccaggag gctggagaat gcggggtctc tgaaggtcct   2220
ctttggcacc ccagaatttg tggctcctga agtgatcaac tatgagccca tcggctacgc   2280
cacagacatg tggagcatcg gggtcatctg ctacatccta gtcagtggcc tttccccctt   2340
catgggagac aacgataacg aaaccttggc caacgttacc tcagccacct gggacttcga   2400
cgacgaggca ttcgatgaga tctccgacga tgccaaggat ttcatcagca atctgctgaa   2460
gaaagatatg aaaaaccgcc tggactgcac gcagtgcctt cagcatccat ggctaatgaa   2520
agataccaag aacatggagg ccaagaaact ctccaaggac cggatgaaga agtacatggc   2580
aagaaggaaa tggcagaaaa cgggcaatgc tgtgagagcc attggaagac tgtcctctat   2640
ggcaatgatc tcagggctca gtggcaggaa atcctcaaca gggtcaccaa ccagcccgct   2700
caatgcagaa aaactagaat ctgaagaaga tgtgtcccaa gctttccttg aggctgttgc   2760
tgaggaaaag cctcatgtaa acccctattt ctctaagacc attcgcgatt tagaagttgt   2820
ggagggaagt gctgctagat tgactgcaa gattgaagga tacccagacc ccgaggttgt   2880
ctggttcaaa gatgaccagt caatcaggga gtcccgccac ttccagatag actacgatga   2940
ggacgggaac tgctctttaa ttattagtga tgtttgcggg gatgacgatg ccaagtacac   3000
ctgcaaggct gtcaacagtc ttggagaagc cacctgcaca gcagagctca ttgtggaaac   3060
gatggaggaa ggtgaagggg aagggaaga ggaagaagag tgaaacaaag ccagagaaaa   3120
gcagtttcta agtcatatta aaaggactat ttctctaaaa ctcaaaaaaa aaaaaaaaa   3180 a                                                                  3181

<210> SEQ ID NO 8
<211> LENGTH: 911
<212> TYPE: DNA
<213> ORGANISM: Homo sapiens

<400> SEQUENCE: 8
ttggagctgt ctcagcctgc agttgcttta tataaaccat ccctttatg ggagttgaag     60 cactgtatga aagggttttt tgtctcatgt tgaccttgtt tagtcacatt aacgcacaca    120
tcagttccag gccccattcc attctctgaa catcttctga cacactgaca gtgctgagca    180
gagcaaggtt gggttcgctc ctctggcaga acctcggctc tcaggaggtc cttgttccag    240
ggaacagctg cttctctggg gctgggctct actccctgca gcccctcgca ctacccagct    300
ggaaccaggg acaacgcctg agtccaaccc tcgtgtctat tttccagaaa acgggcaatg    360
ctgtgagagc cattggaaga ctgtcctcta tggcaatgat ctcagggctc agtggcagga    420
aatcctcaac agggtcacca accagcccgc tcaatgcaga aaaactagaa tctgaagatg    480
tgtcccaagc tttccttgag gctgttgctg aggaaaagcc tcatgtaaaa ccctatttct    540
ctaagaccat tcgcgattta gaagttgtgg agggaagtgc tgctagattt gactgcaaga    600
ttgaaggata cccagacccc gaggttgtct ggttcaaaga tgaccagtca atcagggagt    660
cccgccactt ccagatagac tacgatgagg acgggaactg ctctttaatt attagtgatg    720
tttgcgggga tgacgatgcc aagtacacct gcaaggctgt caacagtctt ggagaagcca    780
```

```
cctgcacagc agagctcatt gtggaaacga tggaggaagg tgaagggaa ggggaagagg      840 aagaagagtg aaacaaagcc agagaaaagc agtttctaag tcatattaaa aggactattt    900
ctctaaaact c                                                          911
```

<210> SEQ ID NO 9
<211> LENGTH: 914
<212> TYPE: DNA
<213> ORGANISM: Homo sapiens

<400> SEQUENCE: 9

```
ttggagctgt ctcagcctgc agttgcttta tataaaccat cccttttatg ggagttgaag     60
cactgtatga aagggttttt tgtctcatgt tgaccttgtt tagtcacatt aacgcacaca    120
tcagttccag gccccattcc attctctgaa catcttctga cacactgaca gtgctgagca    180
gagcaaggtt gggttcgctc ctctggcaga acctcggctc tcaggaggtc cttgttccag    240
ggaacagctg cttctctggg gctgggctct actccctgca gcccctcgca ctacccagct    300
ggaaccaggg acaacgcctg agtccaaccc tcgtgtctat tttccagaaa acgggcaatg    360
ctgtgagagc cattggaaga ctgtcctcta tggcaatgat ctcagggctc agtggcagga    420
aatcctcaac agggtcacca accagcccgc tcaatgcaga aaaactagaa tctgaagaag    480
atgtgtccca gctttccttg aggctgttg ctgaggaaaa gcctcatgta aaccctatt     540 tctctaagac cattcgcgat ttagaagttg tggagggaag tgctgctaga tttgactgca    600
agattgaagg atacccagac cccgaggttg tctggttcaa agatgaccag tcaatcaggg    660
agtcccgcca cttccagata gactacgatg aggacgggaa ctgctcttta attattagtg    720
atgtttgcgg ggatgacgat gccaagtaca cctgcaaggc tgtcaacagt cttggagaag    780
ccacctgcac agcagagctc attgtggaaa cgatggagga aggtgaaggg gaaggggaag    840
aggaagaaga gtgaaacaaa gccagagaaa agcagtttct aagtcatatt aaaaggacta    900
tttctctaaa actc                                                      914
```

<210> SEQ ID NO 10
<211> LENGTH: 405
<212> TYPE: DNA
<213> ORGANISM: Danio rerio
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t

<400> SEQUENCE: 10

```
ggggagagtg gagtcgggac agcggggtct ggacgcgctc tcgaatctgc actccggtga     60 atgcactaa tctgcactgc tgtctgcatg aatgatggc cgatgttcag tttgtttcag     120
gatctcatgt ctccaatact gctctgactc tgggacgagg ctcccccagc aaagagcccc    180 ccgttttac cctcccgccc cgcaataccc gtgtctgcca aggggaact gcgcgccttg     240 agggaaggt acgtggtttc ccagagcctc aggtatgctg gtttaggaat ggcaagctac    300
tgatagcagg agatcattat tctatggaac agagtgtncg cggaacattt tatctggtgg    360
tccaggaggt agaggatgcc cgnggaggac gtttcacttg ttaag                    405
```

<210> SEQ ID NO 11
<211> LENGTH: 1914
<212> TYPE: PRT

<213> ORGANISM: Homo sapiens

<400> SEQUENCE: 11

```
Met Gly Asp Val Lys Leu Val Ala Ser Ser His Ile Ser Lys Thr Ser
1               5                   10                  15

Leu Ser Val Asp Pro Ser Arg Val Asp Ser Met Pro Leu Thr Glu Ala
            20                  25                  30

Pro Ala Phe Ile Leu Pro Pro Arg Asn Leu Cys Ile Lys Glu Gly Ala
        35                  40                  45

Thr Ala Lys Phe Glu Gly Arg Val Arg Gly Tyr Pro Glu Pro Gln Val
    50                  55                  60

Thr Trp His Arg Asn Gly Gln Pro Ile Thr Ser Gly Gly Arg Phe Leu
65                  70                  75                  80

Leu Asp Cys Gly Ile Arg Gly Thr Phe Ser Leu Val Ile His Ala Val
                85                  90                  95

His Glu Glu Asp Arg Gly Lys Tyr Thr Cys Glu Ala Thr Asn Gly Ser
            100                 105                 110

Gly Ala Arg Gln Val Thr Val Glu Leu Thr Val Glu Gly Ser Phe Ala
        115                 120                 125

Lys Gln Leu Gly Gln Pro Val Val Ser Lys Thr Leu Gly Asp Arg Phe
130                 135                 140

Ser Ala Ser Ala Val Glu Thr Arg Pro Ser Ile Trp Gly Glu Cys Pro
145                 150                 155                 160

Pro Lys Phe Ala Thr Lys Leu Gly Arg Val Val Val Lys Glu Gly Gln
                165                 170                 175

Met Gly Arg Phe Ser Cys Lys Ile Thr Gly Arg Pro Gln Pro Gln Val
            180                 185                 190

Thr Trp Leu Lys Gly Asn Val Pro Leu Gln Pro Ser Ala Arg Val Ser
        195                 200                 205

Val Ser Glu Lys Asn Gly Met Gln Val Leu Glu Ile His Gly Val Asn
    210                 215                 220

Gln Asp Asp Val Gly Val Tyr Thr Cys Leu Val Val Asn Gly Ser Gly
225                 230                 235                 240

Lys Ala Ser Met Ser Ala Glu Leu Ser Ile Gln Gly Leu Asp Ser Ala
                245                 250                 255

Asn Arg Ser Phe Val Arg Glu Thr Lys Ala Thr Asn Ser Asp Val Arg
            260                 265                 270

Lys Glu Val Thr Asn Val Ile Ser Lys Glu Ser Lys Leu Asp Ser Leu
        275                 280                 285

Glu Ala Ala Ala Lys Ser Lys Asn Cys Ser Ser Pro Gln Arg Gly Gly
    290                 295                 300

Ser Pro Pro Trp Ala Ala Asn Ser Gln Pro Gln Pro Pro Arg Glu Ser
305                 310                 315                 320

Lys Leu Glu Ser Cys Lys Asp Ser Pro Arg Thr Ala Pro Gln Thr Pro
                325                 330                 335

Val Leu Gln Lys Thr Ser Ser Ser Ile Thr Leu Gln Ala Ala Arg Val
            340                 345                 350

Gln Pro Glu Pro Arg Ala Pro Gly Leu Gly Val Leu Ser Pro Ser Gly
        355                 360                 365

Glu Glu Arg Lys Arg Pro Ala Pro Pro Arg Pro Ala Thr Phe Pro Thr
    370                 375                 380

Arg Gln Pro Gly Leu Gly Ser Gln Asp Val Val Ser Lys Ala Ala Asn
385                 390                 395                 400

Arg Arg Ile Pro Met Glu Gly Gln Arg Asp Ser Ala Phe Pro Lys Phe
```

-continued

```
                    405                 410                 415
Glu Ser Lys Pro Gln Ser Gln Glu Val Lys Glu Asn Gln Thr Val Lys
                420                 425                 430

Phe Arg Cys Glu Val Ser Gly Ile Pro Lys Pro Glu Val Ala Trp Phe
            435                 440                 445

Leu Glu Gly Thr Pro Val Arg Arg Gln Glu Gly Ser Ile Glu Val Tyr
        450                 455                 460

Glu Asp Ala Gly Ser His Tyr Leu Cys Leu Leu Lys Ala Arg Thr Arg
465                 470                 475                 480

Asp Ser Gly Thr Tyr Ser Cys Thr Ala Ser Asn Ala Gln Gly Gln Val
                485                 490                 495

Ser Cys Ser Trp Thr Leu Gln Val Glu Arg Leu Ala Val Met Glu Val
            500                 505                 510

Ala Pro Ser Phe Ser Ser Val Leu Lys Asp Cys Ala Val Ile Glu Gly
        515                 520                 525

Gln Asp Phe Val Leu Gln Cys Ser Val Arg Gly Thr Pro Val Pro Arg
530                 535                 540

Ile Thr Trp Leu Leu Asn Gly Gln Pro Ile Gln Tyr Ala Arg Ser Thr
545                 550                 555                 560

Cys Glu Ala Gly Val Ala Glu Leu His Ile Gln Asp Ala Leu Pro Glu
                565                 570                 575

Asp His Gly Thr Tyr Thr Cys Leu Ala Glu Asn Ala Leu Gly Gln Val
            580                 585                 590

Ser Cys Ser Ala Trp Val Thr Val His Glu Lys Lys Ser Ser Arg Lys
        595                 600                 605

Ser Glu Tyr Leu Leu Pro Val Ala Pro Ser Lys Pro Thr Ala Pro Ile
    610                 615                 620

Phe Leu Gln Gly Leu Ser Asp Leu Lys Val Met Asp Gly Ser Gln Val
625                 630                 635                 640

Thr Met Thr Val Gln Val Ser Gly Asn Pro Pro Glu Val Ile Trp
                645                 650                 655

Leu His Asn Gly Asn Glu Ile Gln Glu Ser Glu Asp Phe His Phe Glu
                660                 665                 670

Gln Arg Gly Thr Gln His Ser Leu Trp Ile Gln Glu Val Phe Pro Glu
        675                 680                 685

Asp Thr Gly Thr Tyr Thr Cys Glu Ala Trp Asn Ser Ala Gly Glu Val
            690                 695                 700

Arg Thr Gln Ala Val Leu Thr Val Gln Glu Pro His Asp Gly Thr Gln
705                 710                 715                 720

Pro Trp Phe Ile Ser Lys Pro Arg Ser Val Thr Ala Ser Leu Gly Gln
            725                 730                 735

Ser Val Leu Ile Ser Cys Ala Ile Ala Gly Asp Pro Phe Pro Thr Val
                740                 745                 750

His Trp Leu Arg Asp Gly Lys Ala Leu Cys Lys Asp Thr Gly His Phe
            755                 760                 765

Glu Val Leu Gln Asn Glu Asp Val Phe Thr Leu Val Leu Lys Lys Val
        770                 775                 780

Gln Pro Trp His Ala Gly Gln Tyr Glu Ile Leu Leu Lys Asn Arg Val
785                 790                 795                 800

Gly Glu Cys Ser Cys Gln Val Ser Leu Met Leu Gln Asn Ser Ser Ala
                805                 810                 815

Arg Ala Leu Pro Arg Gly Arg Glu Pro Ala Ser Cys Glu Asp Leu Cys
            820                 825                 830
```

```
Gly Gly Gly Val Gly Ala Asp Gly Gly Gly Ser Asp Arg Tyr Gly Ser
            835                 840                 845

Leu Arg Pro Gly Trp Pro Ala Arg Gly Gln Gly Trp Leu Glu Glu Glu
            850                 855                 860

Asp Gly Glu Asp Val Arg Gly Val Leu Lys Arg Arg Val Glu Thr Arg
865                 870                 875                 880

Gln His Thr Glu Glu Ala Ile Arg Gln Gln Glu Val Glu Gln Leu Asp
                885                 890                 895

Phe Arg Asp Leu Leu Gly Lys Lys Val Ser Thr Lys Thr Leu Ser Glu
            900                 905                 910

Asp Asp Leu Lys Glu Ile Pro Ala Glu Gln Met Asp Phe Arg Ala Asn
            915                 920                 925

Leu Gln Arg Gln Val Lys Pro Lys Thr Val Ser Glu Glu Glu Arg Lys
            930                 935                 940

Val His Ser Pro Gln Gln Val Asp Phe Arg Ser Val Leu Ala Lys Lys
945                 950                 955                 960

Gly Thr Ser Lys Thr Pro Val Pro Glu Lys Val Pro Pro Lys Pro
                965                 970                 975

Ala Thr Pro Asp Phe Arg Ser Val Leu Gly Gly Lys Lys Leu Pro
            980                 985                 990

Ala Glu Asn Gly Ser Ser Ser Ala Glu Thr Leu Asn Ala Lys Ala Val
            995                 1000                1005

Glu Ser Ser Lys Pro Leu Ser Asn Ala Gln Pro Ser Gly Pro Leu
            1010                1015                1020

Lys Pro Val Gly Asn Ala Lys Pro Ala Glu Thr Leu Lys Pro Met
            1025                1030                1035

Gly Asn Ala Lys Pro Ala Glu Thr Leu Lys Pro Met Gly Asn Ala
            1040                1045                1050

Lys Pro Asp Glu Asn Leu Lys Ser Ala Ser Lys Glu Glu Leu Lys
            1055                1060                1065

Lys Asp Val Lys Asn Asp Val Asn Cys Lys Arg Gly His Ala Gly
            1070                1075                1080

Thr Thr Asp Asn Glu Lys Arg Ser Glu Ser Gln Gly Thr Ala Pro
            1085                1090                1095

Ala Phe Lys Gln Lys Leu Gln Asp Val His Val Ala Glu Gly Lys
            1100                1105                1110

Lys Leu Leu Leu Gln Cys Gln Val Ser Ser Asp Pro Pro Ala Thr
            1115                1120                1125

Ile Ile Trp Thr Leu Asn Gly Lys Thr Leu Lys Thr Thr Lys Phe
            1130                1135                1140

Ile Ile Leu Ser Gln Glu Gly Ser Leu Cys Ser Val Ser Ile Glu
            1145                1150                1155

Lys Ala Leu Pro Glu Asp Arg Gly Leu Tyr Lys Cys Val Ala Lys
            1160                1165                1170

Asn Asp Ala Gly Gln Ala Glu Cys Ser Cys Gln Val Thr Val Asp
            1175                1180                1185

Asp Ala Pro Ala Ser Glu Asn Thr Lys Ala Pro Glu Met Lys Ser
            1190                1195                1200

Arg Arg Pro Lys Ser Ser Leu Pro Pro Val Leu Gly Thr Glu Ser
            1205                1210                1215

Asp Ala Thr Val Lys Lys Lys Pro Ala Pro Lys Thr Pro Pro Lys
            1220                1225                1230

Ala Ala Met Pro Pro Gln Ile Ile Gln Phe Pro Glu Asp Gln Lys
            1235                1240                1245
```

```
Val Arg Ala Gly Glu Ser Val Glu Leu Phe Gly Lys Val Thr Gly
    1250                1255                1260
Thr Gln Pro Ile Thr Cys Thr Trp Met Lys Phe Arg Lys Gln Ile
    1265                1270                1275
Gln Glu Ser Glu His Met Lys Val Glu Asn Ser Glu Asn Gly Ser
    1280                1285                1290
Lys Leu Thr Ile Leu Ala Ala Arg Gln Glu His Cys Gly Cys Tyr
    1295                1300                1305
Thr Leu Leu Val Glu Asn Lys Leu Gly Ser Arg Gln Ala Gln Val
    1310                1315                1320
Asn Leu Thr Val Val Asp Lys Pro Asp Pro Pro Ala Gly Thr Pro
    1325                1330                1335
Cys Ala Ser Asp Ile Arg Ser Ser Ser Leu Thr Leu Ser Trp Tyr
    1340                1345                1350
Gly Ser Ser Tyr Asp Gly Gly Ser Ala Val Gln Ser Tyr Ser Ile
    1355                1360                1365
Glu Ile Trp Asp Ser Ala Asn Lys Thr Trp Lys Glu Leu Ala Thr
    1370                1375                1380
Cys Arg Ser Thr Ser Phe Asn Val Gln Asp Leu Leu Pro Asp His
    1385                1390                1395
Glu Tyr Lys Phe Arg Val Arg Ala Ile Asn Val Tyr Gly Thr Ser
    1400                1405                1410
Glu Pro Ser Gln Glu Ser Glu Leu Thr Thr Val Gly Glu Lys Pro
    1415                1420                1425
Glu Glu Pro Lys Asp Glu Val Glu Val Ser Asp Asp Asp Glu Lys
    1430                1435                1440
Glu Pro Glu Val Asp Tyr Arg Thr Val Thr Ile Asn Thr Glu Gln
    1445                1450                1455
Lys Val Ser Asp Phe Tyr Asp Ile Glu Glu Arg Leu Gly Ser Gly
    1460                1465                1470
Lys Phe Gly Gln Val Phe Arg Leu Val Glu Lys Lys Thr Arg Lys
    1475                1480                1485
Val Trp Ala Gly Lys Phe Phe Lys Ala Tyr Ser Ala Lys Glu Lys
    1490                1495                1500
Glu Asn Ile Arg Gln Glu Ile Ser Ile Met Asn Cys Leu His His
    1505                1510                1515
Pro Lys Leu Val Gln Cys Val Asp Ala Phe Glu Glu Lys Ala Asn
    1520                1525                1530
Ile Val Met Val Leu Glu Ile Val Ser Gly Gly Glu Leu Phe Glu
    1535                1540                1545
Arg Ile Ile Asp Glu Asp Phe Glu Leu Thr Glu Arg Glu Cys Ile
    1550                1555                1560
Lys Tyr Met Arg Gln Ile Ser Glu Gly Val Glu Tyr Ile His Lys
    1565                1570                1575
Gln Gly Ile Val His Leu Asp Leu Lys Pro Glu Asn Ile Met Cys
    1580                1585                1590
Val Asn Lys Thr Gly Thr Arg Ile Lys Leu Ile Asp Phe Gly Leu
    1595                1600                1605
Ala Arg Arg Leu Glu Asn Ala Gly Ser Leu Lys Val Leu Phe Gly
    1610                1615                1620
Thr Pro Glu Phe Val Ala Pro Glu Val Ile Asn Tyr Glu Pro Ile
    1625                1630                1635
Gly Tyr Ala Thr Asp Met Trp Ser Ile Gly Val Ile Cys Tyr Ile
```

-continued

```
            1640                  1645                  1650
Leu Val Ser Gly Leu Ser Pro Phe Met Gly Asp Asn Asp Asn Glu
        1655                1660                1665

Thr Leu Ala Asn Val Thr Ser Ala Thr Trp Asp Phe Asp Asp Glu
        1670                1675                1680

Ala Phe Asp Glu Ile Ser Asp Asp Ala Lys Asp Phe Ile Ser Asn
        1685                1690                1695

Leu Leu Lys Lys Asp Met Lys Asn Arg Leu Asp Cys Thr Gln Cys
        1700                1705                1710

Leu Gln His Pro Trp Leu Met Lys Asp Thr Lys Asn Met Glu Ala
        1715                1720                1725

Lys Lys Leu Ser Lys Asp Arg Met Lys Lys Tyr Met Ala Arg Arg
        1730                1735                1740

Lys Trp Gln Lys Thr Gly Asn Ala Val Arg Ala Ile Gly Arg Leu
        1745                1750                1755

Ser Ser Met Ala Met Ile Ser Gly Leu Ser Gly Arg Lys Ser Ser
        1760                1765                1770

Thr Gly Ser Pro Thr Ser Pro Leu Asn Ala Glu Lys Leu Glu Ser
        1775                1780                1785

Glu Glu Asp Val Ser Gln Ala Phe Leu Glu Ala Val Ala Glu Glu
        1790                1795                1800

Lys Pro His Val Lys Pro Tyr Phe Ser Lys Thr Ile Arg Asp Leu
        1805                1810                1815

Glu Val Val Glu Gly Ser Ala Ala Arg Phe Asp Cys Lys Ile Glu
        1820                1825                1830

Gly Tyr Pro Asp Pro Glu Val Val Trp Phe Lys Asp Asp Gln Ser
        1835                1840                1845

Ile Arg Glu Ser Arg His Phe Gln Ile Asp Tyr Asp Glu Asp Gly
        1850                1855                1860

Asn Cys Ser Leu Ile Ile Ser Asp Val Cys Gly Asp Asp Asp Ala
        1865                1870                1875

Lys Tyr Thr Cys Lys Ala Val Asn Ser Leu Gly Glu Ala Thr Cys
        1880                1885                1890

Thr Ala Glu Leu Ile Val Glu Thr Met Glu Glu Gly Glu Gly Glu
        1895                1900                1905

Gly Glu Glu Glu Glu Glu
        1910
```